United States Patent [19]
Yoshida et al.

[11] Patent Number: 6,150,351
[45] Date of Patent: Nov. 21, 2000

[54] CEPHEM COMPOUNDS AND PHARMACEUTICAL USE THEREOF

[75] Inventors: Yoshiki Yoshida, Suita; Shinya Okuda, Kawanishi; Hiroshi Sasaki, Takarazuka; Keiji Matsuda, Takatsuki; Hisashi Takasugi, Sakai, all of Japan

[73] Assignee: Fujisawa Pharmaceutical Co., Ltd., Osaka, Japan

[21] Appl. No.: 09/125,044

[22] PCT Filed: Feb. 5, 1997

[86] PCT No.: PCT/JP97/00280

§ 371 Date: Aug. 12, 1998

§ 102(e) Date: Aug. 12, 1998

[87] PCT Pub. No.: WO97/29111

PCT Pub. Date: Aug. 14, 1997

[30] Foreign Application Priority Data

Feb. 12, 1996 [AU] Australia ................................ PN8011

[51] Int. Cl.⁷ ........................ A61K 31/546; A61P 31/04; C07D 501/59
[52] U.S. Cl. .......................... 514/204; 540/224; 540/225; 540/226; 540/227
[58] Field of Search .................... 514/203, 204, 514/205, 206; 540/224, 225, 226, 227

[56] References Cited

U.S. PATENT DOCUMENTS 5,162,521  11/1992  Farina ........................ 540/226

FOREIGN PATENT DOCUMENTS

| 9008 | 3/1980 | European Pat. Off. . |
|---|---|---|
| 268307 | 5/1988 | European Pat. Off. . |
| 507124 | 10/1992 | European Pat. Off. . |
| 2537974 | 3/1976 | Germany . |
| 2555858 | 6/1976 | Germany . |
| 2-134385 | 5/1990 | Japan . |
| 8-151386 | 6/1996 | Japan . |
| 95/26966 | 10/1995 | WIPO . |
| 96/17850 | 6/1996 | WIPO . |

*Primary Examiner*—Mark L. Berch
*Attorney, Agent, or Firm*—Oblon, Spivak, McClelland, Maier & Neustadt, P.C.

[57] ABSTRACT

This invention relates to new cephem compound represented by the following general formula (I):

$$R^1-\underset{O}{\underset{\|}{C}}-\underset{H}{\underset{|}{N}}\begin{array}{c}\text{(cephem nucleus)}\end{array}S-R^2$$
(I)

wherein each symbol is as defined in the specification or a salt thereof, which has antimicrobial activity against *Helicobacter pylori*, and are useful as anti-*Helicobacter pylori* agents, anti-gastritis agents, anti-ulcer agents and anti-cancer agents.

7 Claims, No Drawings

CEPHEM COMPOUNDS AND PHARMACEUTICAL USE THEREOF

This application is a 371 application of PCT/JP97/00280, filed Feb. 5, 1997.

FIELD OF THE INVENTION

This invention relates to new cephem compounds and pharmaceutically acceptable salt thereof.

More particularly, it relates to new cephem compounds and salts thereof, which have antimicrobial activity against *Helicobacter pylori*, to a pharmaceutical composition comprising said cephem compound or a pharmaceutically acceptable salt thereof and to a method for the prophylaxis and/or treatment of ulcer and the prophylaxis of stomach cancer in human being and animals.

BACKGROUND ART

At present, acid secretion inhibitors such as $H_2$-blocker and proton pump inhibitor, and mucosalprotective factor enhancers, have been mainly used for the treatment of peptic ulcers such as gastric ulcer and duodenal ulcer. While the use of $H_2$-blocker and proton pump inhibitor shortens treatment period, the problem of possible recurrence of the disease still remains to be solved.

*Helicobacter pylori* (*H. pylori*) is a Gram negative bacterium found in the mucous layer on the gastric epithelium of humans, and infection with *H. pylori* has been found to induce gastrointestinal diseases, such as chronic gastritis and peptic ulcer (e.g., gastric ulcer and duodenal ulcer). There are an increasing number of reports on the effectiveness of the eradication of *H. pylori* for treating intractable ulcers and prevention of ulcer recurrence. The drug having an antimicrobial action on *H. pylori* is useful for the treatment and/or prevention of gastritis and ulcer, and a new drug having such pharmacological action is desired.

DISCLOSURE OF THE INVENTION

One object of this invention is to provide new cephem compounds and salts thereof, which have antimicrobial activity against *Helicobacter pylori*.

The cephem compounds and salts thereof are useful as anti-*Helicobacter pylori* agents, anti-gastritis agents, anti-ulcer agents and anti-cancer agents. The cephem compounds and salts thereof may be used as anti-*Helicobacter pylori* agents, anti-gastritis agents, anti-ulcer agents and anti-cancer agents in combination with an acid secretion inhibitor such as an $H_2$-blocker and a proton pump inhibitor.

A further object of this invention is to provide a pharmaceutical composition for the prophylactic and/or therapeutic treatment of diseases caused by *Helicobacter pylori* infection in human being or animals, comprising, as an active ingredient, said cephem compound or a pharmaceutically acceptable salt thereof.

A further object of this invention is to provide a therapeutical method for the prophylaxis and/or treatment of the diseases caused by *Helicobacter pylori* infection such as gastritis, ulcer [e.g. peptic ulcer (e.g. gastric ulcer, duodenal ulcer, anastomotic ulcer, etc.), etc.], MALT lymphoma, non-ulcer dyspepsia, and stomach cancer in human being and animals.

The cephem compounds in the present invention can be represented by the following general formula (I):

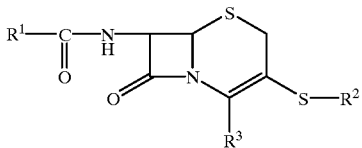

wherein $R^1$ is aryl(lower)alkyl which may have 1 to 3 suitable substituent(s) selected from the group consisting of lower alkyl which may form a ring together with the carbon atom said lower alkyl is attached to, hydroxy and halogen;

heterocyclic(lower)alkyl which may have 1 to 3 suitable substituent(s) selected from the group consisting of lower alkenyl, lower alkylidene, halogen, amino and protected amino; or cyano(lower)alkenylthio(lower)alkyl;

$R^2$ is heterocyclic group which has 1 to 3 suitable substituent(s) selected from the group consisting of acyl(lower)alkyl, hydroxy(lower)alkyl, mono or di(lower)alkylamino(lower)alkyl, amino(lower)alkyl, protected amino(lower)alkyl, acyl, acylamino and aryl having carboxy, in which heterocyclic group may have additionally lower alkyl;

pyridyl(lower)alkyl;

pyrazolylethyl which may have aryl(lower)alkyl;

thiadiazolyl(lower)alkyl;

5-aminothiazolyl;

thiadiazolyl having lower alkyl;

heterocyclic(lower)alkenyl which may have 1 to 3 suitable substituent(s); or heterocyclicthio(lower)alkyl which may have 1 to 3 suitable substituent(s); and $R^3$ is carboxy or protected carboxy, with proviso that 1) when $R^1$ is aryl(lower)alkyl and $R^2$ is thiadiazolyl having lower alkyl, then $R^3$ is acyloxy(lower) alkoxycarbonyl, 2) when $R^1$ is aryl(lower)alkyl having halogen, then $R^2$ is not thiadiazolyl having lower alkyl, 3) when $R^1$ is aminothiazolyl(lower)alkyl, then $R^2$ is not thiadiazolyl having lower alkyl.

The cephem compound (I) or a salt thereof can be prepared by processes as illustrated in the following reaction schemes.

Process 1

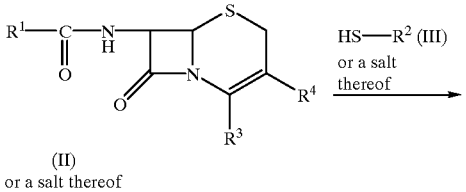

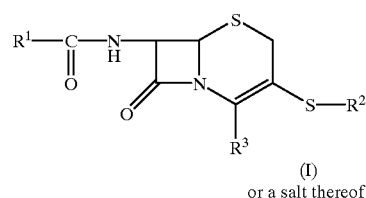

-continued

Process 2

(Ia) or a salt thereof
→ Elimination of the carboxy-protective group →
(Ib) or a salt thereof Process 3

H$_2$N—[β-lactam]—S—R$^2$ with R$^3$
+ R$^1$—COOH (V) or its reactive derivative at the carboxy group or a salt thereof
→ (I) or a salt thereof Process 4

(Ib) or its reactive derivative at the carboxy group or a salt thereof
→ protecting reaction of carboxy →
(Ia) or a salt thereof wherein R$^1$, R$^2$ and R$^3$ are each as defined above,
R$^4$ is a leaving group, and
R$^5$ is protected carboxy.

The starting compounds (II) and (IV) or a salt thereof can be prepared by processes as illustrated in the following schemes.

Process A (VI) or a salt thereof
→ Elimination of the amino-protective group →
(VII) or a salt thereof Process B (VII) or its reactive derivative at the amino group or a salt thereof
+ R$^1$—COOH (V) or its reactive derivatives at the carboxy group or a salt thereof
→ (II) or a salt thereof Process C (VI) or a salt thereof
+ HS—R$^2$ (III) or a salt thereof
→ (VIII) or a salt thereof Process D (VIII) or a salt thereof
→ Elimination of the amino-protective group →

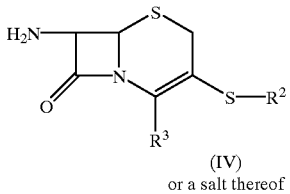

(IV)

or a salt thereof wherein R¹, R², R³ and are each as defined above, and
R⁶ is protected amino.

Suitable examples of the various definitions of the cephem compound (I) of the present invention to be included within the scope of the invention, which are given in the description of the present specification, are explained in detail in the following.

The term "lower" is intended to mean a group having 1 to 6 carbon atoms, preferably 1 to 4 carbon atoms, unless otherwise provided.

Suitable "lower alkyl" and "lower alkyl" moiety in "aryl (lower)alkyl", "heterocyclic(lower)alkyl", "acyl(lower) alkyl", "hydroxy(lower)alkyl", "mono or di(lower) alkylamino(lower)alkyl", "amino(lower)alkyl", "acylamino (lower)alkyl", "phenyl(lower)alkyl", etc. may include straight or branched ones having 1 to 6 carbon atoms, such as methyl, ethyl, propyl, isopropyl, butyl, isobutyl, tert-butyl, pentyl, isopentyl and hexyl, preferable ones having 1 to 4 carbon atoms.

Suitable "halogen" may include chloro, bromo, fluoro and iodo.

Suitable "lower alkenyl" and "lower alkenyl" moiety may include straight or branched alkenyl having 2 to 6 carbon atoms, such as vinyl, 1-propenyl, allyl, isopropenyl, 1-butenyl, 2-butenyl, 1-pentenyl and 2-pentenyl, preferable ones having 2 to 4 carbon atoms.

Suitable "lower alkylidene" may include straight or branched one such as methylene, ethylidene, propylidene, vinylidene, butylidene, isopropylidene, pentylidene, t-butylidene, hexylidene, and the like, in which the preferred one may be $(C_1-C_4)$alkylidene, and the most preferred one may be propylidene.

Suitable "ring" in "lower alkyl which may form a ring together with the carbon atom said lower alkyl is attached to" may be cyclo$(C_3-C_6)$alkyl, such as cyclopropyl, cyclobutyl, cyclopentyl, cyclohexyl, and the like, in which the preferred one may be cyclo$(C_3-C_4)$alkyl, and the most preferred one may be cyclopropyl.

Suitable "aryl" moiety in "aryl(lower)alkyl", may include $(C_6-C_{10})$aryl, such as phenyl, naphthyl, tolyl, xylyl, mesityl and cumenyl, in which more preferred one is phenyl.

Preferable example of "aryl(lower)alkyl" may include mono or di or tri aryl(lower)alkyl such as benzyl, phenethyl, trityl, α-methylbenzyl and naphthylmethyl, in which more preferred one is phenyl(lower)alkyl and the most preferred one is benzyl.

The "lower alkyl" and "aryl" moiety in "aryl(lower)alkyl" each may have 1 to 3 suitable substituent(s), such as lower alkyl which may form a ring together with the carbon atom said lower alkyl is attached to, hydroxy, halogen, and the like.

Suitable "heterocyclic" moiety in "heterocyclic(lower) (lower)alkyl", "heterocyclic group", etc. may include saturated or unsaturated monocyclic or polycyclic heterocyclic group containing at least one hetero-atom such as an oxygen, sulfur, nitrogen atom, and the like, such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, 4,5,6,7-tetrahydrobenzothiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

Suitable "lower alkyl" moiety in "heterocyclic(lower) alkyl" can be referred to aforementioned "lower alkyl", in which the preferred one may be $(C_1-C_4)$alkyl, and the most preferred one may be methyl.

Preferable examples of "heterocyclic(lower)alkyl" for R¹ may include lower alkyl having unsaturated 3 to 8-membered heteromonocyclic group containing 1 to 2 sulfur atom(s), and lower alkyl having unsaturated 3 to 8-membered heteromonocyclic group containing 1 to 2 sulfur atom(s) and 1 to 3 nitrogen atom(s), the more preferred one may be thienyl($C_1$–$C_4$)alkyl, thiazolyl($C_1$–$C_4$) alkyl and thiadiazolyl($C_1$–$C_4$)alkyl, and the most preferred one may be thienylmethyl, thiazolylmethyl and thiadiazolylmethyl.

Preferable example of "heterocyclic group" for $R^2$ may include unsaturated 3 to 8-membered heteromonocyclic group containing 1 to 4 nitrogen atom(s), unsaturated 3 to 8-membered heteromonocyclic group containing 1 to 2 sulfur atom(s) and 1 to 3 nitrogen atom(s) and unsaturated condensed heterocyclic group containing 1 to 2 sulfur atom (s) and 1 to 3 nitrogen atom(s), the more preferred one may be thiadiazolyl, thiazolyl, triazolyl, tetrazolyl and tetrahydrobenzothiazolyl Suitable "acyl" and "acyl" moiety in "acyl(lower)alkyl", "acylamino(lower)alkyl" or "acylamino" may include carboxy, carbamoyl, thiocarbamoyl, aliphatic acyl group and acyl group containing an a romatic ring, which is referred to as aromatic acyl, or heterocyclic ring, which is referred to as heterocyclic acyl.

Suitable example of said acyl may be illustrated as follows:
carboxy;
carbamoyl;
thiocarbamoyl;
aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoy, nonadecanoyl, icosanoyl, etc.); lower or higher alkoxycarbonyl (e.g., methoxycarbonyl, ethoxycarbonyl, t-butoxycarbonyl, t-pentyloxycarbonyl, heptyloxycarbonyl, etc.);
lower or higher alkylsulfonyl (e.g., methylsulfonyl, ethylsulfonyl, etc.);
lower or higher alkoxysulfonyl (e.g., methoxysulfonyl, ethoxysulfonyl, etc.); or the like;
mono or di(lower)alkylaminocarbonyl (e.g., methylaminocarbonyl, dimethylaminocarbonyl, ethylaminocarbonyl, diethylaminocarbonyl, N-methyl-N-ethylaminocarbonyl, propylaminocarbonyl, butylaminocarbonyl, N-ethyl-N-propylaminocarbonyl, etc.);
aromatic acyl such as
aroyl (e.g., benzoyl, toluoyl, naphthoyl, etc.); ar(lower) alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower) alkanoyl (e.g., naphthylacetyl, naphthylpropanoyl, naphthylbutanoyl, etc.), etc.];
ar(lower)alkenoyl [e.g., phenyl(lower)alkenoyl (e.g., phenylpropenoyl, phenylbutenoyl, phenylmethacryloyl, phenylpentenoyi, phenylhexenoyl, etc.), naphthyl(lower) alkenoyl (e.g., naphthylpropenoyl, naphthylbutenoyl, etc.), etc.];
ar(lower)alkoxycarbonyl [e.g., phenyl(lower) alkoxycarbonyl (e.g. benzyloxycarbonyl, etc.), etc.];
aryloxycarbonyl (e.g., phenoxycarbonyl, naphthyloxycarbonyl, etc.);
aryloxy(lower)alkanoyl (e.g., phenoxyacetyl, phenoxypropionyl, etc.);
arylcarbamoyl (e.g., phenylcarbamoyl, etc.); arylthiocarbamoyl (e.g., phenylthiocarbamoyl, etc.);
arylglyoxyloyl (e.g., phenylglyoxyloyl, naphthylglyoxyloyl, etc.);
arylsulfonyl (e.g., phenylsulfonyl, p-tolylsulfonyl, etc.); or the like;
heterocyclic acyl such as
heterocycliccarbonyl;
heterocyclic(lower)alkanoyl (e.g., heterocyclicacetyl, heterocyclicpropanoyl, heterocyclicbutanoyl, heterocyclicpentanoyl, heterocyclichexanoyl, etc.);
heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; heterocyclic(lower)alkylcarbamoyl (e.g., heterocyclicmethylcarbamoyl, heterocyclicethylcarbamoyl, heterocyclicpropylcarbamoyl, heterocyclichexylcarbamoyl, etc.); or the like;
in which suitable "heterocyclic" moiety in the terms "heterocycliccarbonyl", "heterocyclic(lower)alkanoyl, heterocyclic(lower)alkenoyl" and "heterocyclicglyoxyloyl" can be referred to aforementioned "heterocyclic" moiety.

Suitable "cyano(lower)alkenylthio(lower)alkyl" may include cyanovinylthiomethyl, cyanovinylthioethyl, cyanovinylthiopropyl, 3-cyano-1-propenylthiomethyl, 3-cyano-1-propenylthioethyl, cyanoallylthiomethyl and cyanoallylthioethyl, in which more preferred one may be cyano($C_2$–$C_4$)alkenylthio($C_1$–$C_6$)alkyl and the most preferred one may be cyanovinylthiomethyl.

Suitable "lower alkyl" moiety in "acyl(lower)alkyl" can be referred to aforementioned "lower alkyl", in which the preferred one may be ($C_1$–$C_4$)alkyl, and the most preferred one may be methyl and ethyl.

Suitable "acyl" moiety in "acyl(lower)alkyl" can be referred to aforementioned "acyl", in which the preferred one may be carboxy, carbamoyl, mono or di(lower) alkylaminocarbonyl, lower alkoxycarbonyl, N-heterocycliccarbonyl, N-heterocyclic(lower) alkylcarbamoyl and thiocarbamoyl, and the most preferred one may be carboxy, carbamoyl, dimethylaminocarbonyl, ethoxycarbonyl, methoxycarbonyl, morpholinocarbonyl, N-methylcarbamoyl, N-pyridylmethylcarbamoyl and thiocarbamoyl.

Preferable example of "acyl(lower)alkyl" may include acyl($C_1$–$C_4$)alkyl, more preferred one may be carboxymethyl, carboxyethyl, carboxypropyl, carboxyisopropyl, carboxybutyl, carboxy-t-butyl, carbamoylmethyl, carbamoylethyl, carbamoylpropyl, carbamoylisopropyl, carbamoylbutyl, carbamoyl-t-butyl, methylaminocarbonylmethyl, dimethylaminocarbonylmethyl, ethylaminocarbonylmethyl, diethylaminocarbonylethyl, propylaminocarbonylethyl, butylaminocarbonylpropyl, ethoxycarbonylmethyl, morpholinocarbonylmethyl, pyridylmethylcarbamoylmethyl, methoxycarbonylethyl and thiocarbamoylmethyl, and the most preferred one may be carboxymethyl, carbamoylmethyl, dimethylaminocarbonylmethyl, ethoxycarbonylmethyl, morpholinocarbonylmethyl, pyridylmethylcarbamoylmethyl, methoxycarbonylethyl and thiocarbamoylmethyl.

Suitable "lower alkyl" moiety in "hydroxy(lower)alkyl" can be referred to aforementioned "lower alkyl", in which the preferred one may be ($C_1$–$C_4$)alkyl, and the most preferred one may be methyl and ethyl.

Preferable example of "hydroxy(lower)alkyl" may include hydroxy($C_1$–$C_4$)alkyl, more preferred one may be hydroxymethyl, hydroxyethyl, hydroxypropyl, hydroxyisopropyl, hydroxybutyl and hydroxy-t-butyl, and the most preferred one may be hydroxymethyl and hydroxyethyl.

Suitable "lower alkyl" moiety in "mono or di(lower) alkylamino(lower)alkyl" can be referred to aforementioned "lower alkyl", in which the preferred one may be methyl.

Suitable "mono or di lower alkylamino" moiety in "mono or di lower alkylamino(lower)alkyl" may include methylamino, ethylamino, propylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino and N-methyl-N-ethylamino, in which the preferred one may be mono or di($C_1$–$C_4$)alkylamino, and the most preferred one may be dimethylamino.

Preferable example of "mono or di(lower)alkylamino (lower)alkyl" may include mono or di($C_1$–$C_4$)alkylamino ($C_1$–$C_4$)alkyl, more preferred one may be methylaminomethyl, ethylaminoethyl, propylaminomethyl, isopropylaminopropyl, butylaminomethyl, tert-butylaminoethyl, isobutylaminobutyl, dimethylaminomethyl, diethylaminoethyl, dipropylaminomethyl, dibutylaminopropyl, diisopropylaminobutyl, and N-methyl-N-ethylaminomethyl, and the most preferred one may be dimethylaminomethyl.

Suitable "lower alkyl" moiety in "amino(lower)alkyl" can be referred to aforementioned "lower alkyl", in which the preferred one may be ($C_1$–$C_4$)alkyl, and the most preferred one may be methyl.

Preferable example of "amino(lower)alkyl" may include amino($C_1$–$C_4$)alkyl, more preferred one may be aminomethyl, aminoethyl, aminopropyl, aminoisopropyl, aminobutyl and amino-t-butyl, and the most preferred one may be aminomethyl.

Suitable "lower alkyl" moiety in "protected amino(lower) alkyl" for $R^2$ can be referred to aforementioned "lower alkyl", in which the preferred one may be ($C_1$–$C_4$)alkyl, and the most preferred one may be methyl.

Suitable "protected amino" moiety in "protected amino (lower)alkyl" may include an acylamino.

Suitable "acyl" moiety in aforementioned "acylamino" can be referred to aforementioned "acyl", in which preferred one may be lower alkoxycarbonyl, the more preferred one may be ($C_1$–$C_4$)alkoxycarbonyl, and the most preferred one may be t-butoxycarbonyl.

Preferable example of "acylamino(lower)alkyl" may include lower alkoxycarbonylamino(lower)alkyl, more preferred one may be ($C_1$–$C_4$)alkoxycarbonylamino($C_1$–$C_4$) alkyl, and the most preferred one may be t-butoxycarbonylaminomethyl.

Suitable "acyl" moiety in "acylamino" can be referred to aforementioned "acyl", in which preferred one may include carbamoyl and lower alkanoyl, and the most preferred one may be carbamoyl, formyl and acetyl.

Preferable example of "acylamino" may include ureido and lower alkanoylamino, in which the preferred one may be ureido and ($C_1$–$C_4$)alkanoylamino, and the most preferred one may be ureido, formylamino and acetylamino.

Suitable "aryl having carboxy" may include carboxyphenyl, carboxynaphthyl, carboxyanthryl, and the like, in which the most preferred one may be carboxyphenyl.

Suitable "pyridyl(lower)alkyl" may include pyridylmethyl, pyridylethyl, pyridylpropyl, pyridylbutyl, pyridylpentyl, pyridylhexyl, and the like, in which the preferred one may be pyridyl($C_1$–$C_4$)alkyl, and the most preferred one may be pyridylmethyl and pyridylethyl.

Suitable "thiadiazolyl(lower)alkyl" may include thiadiazolylmethyl, thiadiazolylethyl, thiadiazolylpropyl, thiadiazolylbutyl, thiadiazolylpentyl, thiadiazolylhexyl, and the like, in which the preferred one may be thiadiazolyl ($C_1$–$C_4$)alkyl, and the most preferred one may be 1,2,3-thiadiazolylmethyl.

Suitable "heterocyclic" moiety in "heterocyclic(lower) alkenyl" can be referred to aforementioned "heterocyclic" moiety, in which the preferred one may be unsaturated 3 to 8-membered heteromonocyclic group containing 1 to 4 nitrogen atom(s), and the most preferred one may be pyridyl and pyrazolyl.

Suitable "lower alkenyl" moiety in "heterocyclic(lower) alkenyl" can be referred to aforementioned "lower alkenyl" moiety, in which the preferred one may be ($C_2$–$C_4$)alkenyl, and the most preferred one may be vinyl.

Preferable "heterocyclic(lower)alkenyl" moiety may include ($C_2$–$C_4$)alkenyl having unsaturated 3 to 8-membered heteromonocyclic group containing 1 to 4 nitrogen atom(s), in which the preferred one may be pyridylvinyl and pyrazolylvinyl.

Suitable "suitable substituent" in "heterocyclic(lower) alkenyl which may have 1 to 3 suitable substituent(s)" may include aforementioned "acyl", in which the preferred one may be aryl(lower)alkylcarbonyl, and the more preferred one may be phenyl($C_1$–$C_4$)alkylcarbonyl, and the most preferred one may be benzylcarbonyl.

Suitable "heterocyclic" moiety in "heterocyclicthio (lower)alkyl which may have 1 to 3 suitable substituent(s)" can be referred to aforementioned "heterocyclic" moiety, in which the preferred one may be unsaturated 3 to 8-membered heteromonocyclic group containing 1 to 2 sulfur atom(s) and 1 to 3 nitrogen atom(s), and the most preferred one may be thiazolyl.

Preferable "heterocyclicthio(lower)alkyl" moiety may include thio($C_1$–$C_4$)alkyl having unsaturated 3 to 8-membered heteromonocyclic group containing 1 to 2 sulfur atom(s) and 1 to 3 nitrogen atom(s), in which the preferred one may be thiazolylthiomethyl.

Suitable "suitable substituent(s)" in "heterocyclicthio (lower)alkyl which may have 1 to 3 suitable substituent(s)" may include aforementioned "acyl(lower)alkyl", in which the preferred one may be carbamoyl($C_1$–$C_4$)alkyl, and the most preferred one may be carbamoylmethyl.

Suitable "protected carboxy" may include carboxy group protected by conventional protective group such as an esterified carboxy group, and the like, and concrete examples may be substituted or unsubstituted lower alkoxycarbonyl (e.g. methoxycarbonyl, ethoxycarbonyl, propoxycarbonyl, butoxycarbonyl, tert-butoxycarbonyl, pentyloxycarbonyl, hexyloxycarbonyl, 2-(dimethylamino) ethoxycarbonyl, 2-iodoethoxycarbonyl, 2,2,2-trichloroethoxycarbonyl), substituted or unsubstituted aryloxycarbonyl (e.g. phenoxycarbonyl, 4-nitrophenoxycarbonyl, 2-naphthyloxycarbonyl), and substituted or unsubstituted aryl(lower)alkoxycarbonyl, for example, mono or di or triphenyl(lower)alkoxycarbonyl which may be substituted with nitro (e.g. benzyloxycarbonyl, phenethyloxycarbonyl, benzhydryloxycarbonyl, 4-nitrobenzyloxycarbonyl) acyloxy(lower)alkoxycarbonyl (e.g. t-butylcarbonyloxymethyloxycarbonyl, 1-t-butylcarbonyloxy-1-methylmethyloxycarbonyl, 1-isopropylcarbonyloxy-1-methylmethyloxycarbonyl, 1-isobutylcarbonyloxy-1-methylmethyloxycarbonyl).

Suitable "leaving group" may include a substituted lower alkoxy such as lower alkoxy(lower)alkoxy (e.g. methoxymethoxy), lower alkoxy(lower)alkoxy(lower) alkoxy (e.g., methoxyethoxymethoxy), a substituted or unsubstituted aryl(lower)alkoxy (e.g. benzyloxy, nitrobenzyloxy); acyloxy such as lower alkanoyloxy (e.g.

acetoxy, propionyloxy, pivaloyloxy), aroyloxy (e.g. benzoyloxy, fluorenecarbonyloxy), lower alkoxycarbonyloxy (e.g. methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy), a substituted or unsubstituted aryl (lower)alkoxycarbonyloxy (e.g. benzyloxycarbonyloxy, bromobenzyloxycarbonyloxy), arenesulfonyloxy (e.g. benzenesulfonyloxy, tosyloxy), alkanesulfonyloxy which may have one or more suitable substituent(s) (e.g. methanesulfonyloxy, trifluoromethanesulfonyloxy, ethanesulfonyloxy); and tri(lower)alkylsilyloxy (e.g. trimethylsilyloxy).

Suitable "protected amino" may include an acylamino or an amino group substituted by a conventional protecting group such as ar(lower)alkyl which may have suitable substituent(s) (e.g., benzyl, trityl, etc.) and the like.

Suitable "acyl" moiety in abovementioned "acylamino" can be referred to aforementioned "acyl", in which the preferred one may be lower alkanoyl, and the most preferred one may be formyl and acetyl.

Preferable "protected amino" may include acylamino, in which the preferred one may be lower alkanoylamino, and the most preferred one may be formylamino and acetylamino.

Suitable salts of the object compound (I) are pharmaceutically acceptable salts such as conventional non-toxic salts and include an organic acid addition salt (e.g. formate, acetate, trifluoroacetate, maleate, tartrate, methanesulfonate, benzenesulfonate, p-toluenesulfonate), an inorganic acid addition salt (e.g. hydrochloride, hydrobromide, sulfate, phosphate), an alkali metal salt (e.g. sodium salt, potassium salt) and an alkaline earth metal salt (e.g. calcium salt, magnesium salt).

Suitable examples of the salts of the compounds (II), (III), (IV), (V), (VI), (VII) and (VIII) in Processes 1 to 4 and Processes A to D are to be referred to those as exemplified for the object compound (I).

Particularly, the preferred examples of the compound (I) in the present invention are as follows: the compound (I), wherein $R^1$ is aryl(lower)alkyl which may have 1 to 3 suitable substituent(s) selected from the group consisting of lower alkyl which may form a ring together with the carbon atom said lower alkyl is attached to, hydroxy and halogen;
lower alkyl having unsaturated 3 to 8-membered heteromonocyclic group containing 1 to 2 sulfur atom(s) which may have 1 to 3 suitable substituent(s) selected from the group consisting of lower alkenyl, lower alkylidene, halogen, amino and acylamino; or cyano(lower)alkenylthio(lower)alkyl;

$R^2$ is unsaturated heteromonocyclic group containing 1 to 2 sulfur atom(s) and 1 to 3 nitrogen atom(s) which has 1 to 3 suitable substituent(s) selected from the group consisting of acyl(lower)alkyl, hydroxy(lower)alkyl, mono or di(lower)alkylamino(lower)alkyl, amino (lower)alkyl, acylamino(lower)alkyl, acyl, acylamino and aryl having carboxy, in which heterocyclic monocyclic group may have additionally lower alkyl;
pyridyl(lower)alkyl;
pyrazolylethyl which may have aryl(lower)alkyl;
thiadiazolyl(lower)alkyl;
5-aminothiazolyl;
thiadiazolyl having lower alkyl;
unsaturated 3 to 8-membered heteromonocyclic group containing 1 to 4 nitrogen atom(s) which has acyl (lower)alkyl;
lower alkenyl having unsaturated 3 to 8-membered heteromonocyclic group containing 1 to 4 nitrogen atom(s), which may have acyl; or
lower alkylthio having unsaturated 3 to 8-membered heteromonocyclic group containing 1 to 2 sulfur atom(s) and 1 to 3 nitrogen atom(s) which may have acyl(lower)alkyl; and $R^3$ is carboxy or protected carboxy; with proviso that
1) when $R^1$ is aryl(lower)alkyl and $R^2$ is thiadiazolyl having lower alkyl, then $R^3$ is acyloxy(lower) alkoxycarbonyl,
2) when $R^1$ is aryl(lower)alkyl having halogen, then $R^2$ is not thiadiazolyl having lower alkyl,
3) when $R^1$ is aminothiazolyl(lower)alkyl, then $R^2$ is not thiadiazolyl having lower alkyl, more preferred one is the compound (I), wherein $R^1$ is phenyl(lower)alkyl which may have 1 to 3 suitable substituent(s) selected from the group consisting of lower alkyl which may form a 3 to 6-membered ring together with the carbon atom said lower alkyl is attached to, hydroxy and halogen;
thienyl(lower)alkyl, thiazolyl(lower)alkyl or thiadiazolyl(lower)alkyl, each of which may have 1 to 3 suitable substituent(s) selected from the group consisting of lower alkenyl, lower alkylidene, halogen, amino and acylamino; or
cyano(lower)alkenylthio(lower)alkyl;

$R^2$ is thiazolyl which has 1 to 3 suitable substituent(s) selected from the group consisting of acyl(lower)alkyl, hydroxy(lower)alkyl, acyl, acylamino and phenyl having carboxy, in which thiazolyl may have additionally lower alkyl;
thiadiazolyl which has 1 to 3 suitable substituent(s) selected from the group consisting of lower alkyl, hydroxy(lower)alkyl, mono or di(lower)alkylamino (lower)alkyl and amino(lower)alkyl;
pyridyl(lower)alkyl;
pyrazolylethyl which may have trityl;
thiadiazolyl(lower)alkyl;
5-aminothiazolyl;
5-methyl-1,3,4-thiadiazolyl;
triazolyl which has acyl(lower)alkyl;
tetrazolyl which has acyl(lower)alkyl;
lower alkenyl having unsaturated 3 to 8-membered heteromonocyclic group containing 1 to 4 nitrogen atom(s) which may have acyl; or
lower alkenylthio having unsaturated heteromonocyclic group containing 1 to 2 sulfur atom(s) and 1 to 3 nitrogen atom(s) which may have acyl(lower) alkyl; and $R^3$ is carboxy or protected carboxy;

much more preferred one is the compound (I), wherein $R^1$ is phenyl(lower)alkyl, thienyl(lower)alkyl, thiazolyl (lower)alkyl or thiadiazolyl(lower)alkyl, $R^2$ is thiazolyl which has a suitable substituent selected from the group consisting of carboxy(lower)alkyl, carbamoyl(lower)alkyl, mono or di lower alkylaminocarbonyl(lower)alkyl, hydroxy(lower)alkyl, carbamoyl, morpholinocarbonyl(lower)alkyl, pyridyl (lower)alkylaminocarbonyl(lower)alkyl, lower alkoxycarbonyl(lower)alkyl, thiocarbamoyl(lower) alkyl, ureido and phenyl having carboxy, in which thiazolyl may have additionally lower alkyl;
thiadiazolyl which has a suitable substituent selected from the group consisting of hydroxy(lower)alkyl, di(lower)alkylamino(lower)alkyl, amino(lower)

alkyl, lower alkoxycarbonylamino(lower)alkyl and carboxy(lower)alkyl;
pyridyl(lower)alkyl;
pyrazolylethyl which may have trityl;
thiadiazolyl(lower)alkyl;
5-aminothiazolyl;
5-methyl-1,3,4-thiadiazolyl;
triazolyl which has a suitable substituent selected from the group consisting of carboxy(lower)alkyl and lower alkoxycarbonyl(lower)alkyl;
tetrazolyl which has a carboxy(lower)alkyl;
pyridyl(lower)alkenyl; or
pyrazolyl(lower)alkenyl which has a benzylcarbonyl; and $R^3$ is carboxy or protected carboxy;
one of still much more preferred one is the compound (I), wherein $R^1$ is phenyl(lower)alkyl, $R^2$ is thiazolyl which has a suitable substituent selected from the group consisting of carboxy(lower)alkyl, carbamoyl(lower)alkyl, mono or di lower alkylaminocarbonyl(lower)alkyl, hydroxy(lower)alkyl, carbamoyl, morpholinocarbonyl(lower)alkyl, pyridyl (lower)alkylaminocarbonyl(lower)alkyl, lower alkoxycarbonyl(lower)alkyl, thiocarbamoyl(lower) alkyl, ureido and phenyl having carboxy, in which thiazolyl may have additionally lower alkyl;
thiadiazolyl which has a suitable substituent selected from the group consisting of hydroxy(lower)alkyl, di(lower)alkylamino(lower)alkyl, amino(lower) alkyl, lower alkoxycarbonylamino(lower)alkyl and carboxy(lower)alkyl;
pyridyl(lower)alkyl;
pyrazolylethyl which may have trityl;
thiadiazolyl(lower)alkyl;
5-aminothiazolyl;
5-methyl-1,3,4-thiadiazolyl;
triazolyl which has a suitable substituent selected from the group consisting of carboxy(lower)alkyl and lower alkoxycarbonyl(lower)alkyl;
tetrazolyl which has carboxy(lower)alkyl;
pyridyl(lower)alkenyl; or
pyrazolyl(lower)alkenyl which has a benzylcarbonyl; and $R^3$ is carboxy,
another one of still much more preferred one is the compound (I), wherein $R^1$ is thienyl(lower)alkyl, $R^2$ is thiazolyl which has a suitable substituent selected from the group consisting of carboxy(lower)alkyl and carbamoyl(lower)alkyl, or thiadiazolyl having hydroxy (lower)alkyl, and $R^3$ is carboxy, extremely preferred one is the compound (I), wherein $R^1$ is phenyl(lower)alkyl, $R^2$ is thiazolyl having carboxy(lower)alkyl or thiazolyl having carbamoyl(lower)alkyl, and $R^3$ is carboxy,
another extremely more preferred one is the compound (I), wherein $R^1$ is thienyl(lower)alkyl, $R^2$ is thiazolyl having carboxy(lower)alkyl or thiazolyl having carbamoyl(lower)alkyl, and $R^3$ is carboxy, the most preferred one is the compound (I), wherein $R^1$ is phenyl(lower)alkyl, $R^2$ is thiazolyl having carbamoyl(lower)alkyl, and $R^3$ is carboxy,
another most preferred one is the compound (I), wherein $R^1$ is thienyl(lower)alkyl, $R^2$ is thiazolyl having carbamoyl(lower)alkyl, and $R^3$ is carboxy.

The processes for preparing the cephem compound (I) or a salt thereof in the present invention are explained in detail in the following.

Process 1

The compound (I) or a salt thereof can be prepared by reacting the compound (II) or a salt thereof with the compound (III) or a salt thereof.

Suitable salts of the compound (III) include alkali metal salts (e.g. sodium salt, potassium salt).

The reaction is usually carried out in the presence of a base. Suitable examples of the base include organic bases such as triethylamine, trimethylamine, N,N-diisopropylethylamine, dimethylamine, N-methylmorpholine and pyridine, and inorganic bases such as alkali metal hydroxides (e.g. sodium hydroxide, potassium hydroxide), alkali metal carbonates (e.g. sodium carbonate, potassium carbonate), and alkali metal hydrogencarbonates (e.g. sodium hydrogencarbonate, potassium hydrogencarbonate).

The reaction is usually carried out in a solvent such as water, acetone, acetonitrile, dioxane, tetrahydrofuran, N,N-dimethylformamide, dimethyl sulfoxide, 1,2-dimethoxyethane, a mixture thereof or any other solvent which does not adversely influence the reaction.

The reaction temperature is not critical and the reaction is usually carried out under cooling to heating.

Process 2

The object compound (Ib) or a salt thereof can be prepared by subjecting the compound (Ia) or a salt thereof to an elimination reaction of the carboxy-protective group.

In the present elimination reaction, all conventional methods used for the elimination of the carboxy-protective group, for example, hydrolysis, reduction, elimination using a Lewis acid, etc. are applicable. When the carboxy-protective group is an ester, it can be eliminated by hydrolysis or elimination using Lewis acid. The hydrolysis is preferably carried out in the presence of a base or an acid.

Suitable base includes, for example, inorganic bases such as alkali metal hydroxides (e.g. sodium hydroxide, potassium hydroxide), alkaline earth metal hydroxides (e.g. magnesium hydroxide, calcium hydroxide), alkali metal carbonates (e.g. sodium carbonate, potassium carbonate), alkaline earth metal carbonates (e.g. magnesium carbonate, calcium carbonate), alkali metal hydrogencarbonate (e.g. sodium hydrogencarbonate, potassium hydrogencarbonate), alkali metal acetates (e.g. sodium acetate, potassium acetate), alkaline earth metal phosphates (e.g. magnesium phosphate, calcium phosphate), and alkali metal hydrogen phosphates (e.g. disodium hydrogen phosphate, dipotassium hydrogen phosphate); and organic bases such as trialkylamines (e.g. tirmethylamine, triethylamine), picoline, N-methylpyrrolidine, N-methylmorpholine, and 1,5-diazabicyclo[4.3.0]non-5-one, 1,4-diazabicyclo[2.2.2] octane, and 1,5-diazabicyclo[5.4.0]undecene-5. The hydrolysis using a base is often carried out in water or a hydrophilic organic solvent or a mixed solvent thereof.

Suitable acid includes organic acids (e.g. formic acid, acetic acid, propionic acid) and inorganic acids (e.g. hydrochloric acid, hydrobromic acid, sulfuric acid). The present hydrolysis is usually carried out in water or an organic solvent or a mixed solvent thereof.

The reaction temperature is not critical, and it may be selected suitably in accordance with the kind of carboxy protective group and elimination method.

The elimination using a Lewis acid is preferable for eliminating a substituted or unsubstituted aryl(lower)alkyl ester, and carried out by reacting the compound (Ia) or a salt thereof with a Lewis acid. Examples of the Lewis acid are boron trihalides (e.g. boron trichloride, boron trifluoride), titanium tetrahalides (e.g. titanium tetrachloride, titanium tetrabromide), tin tetrahalides (e.g. tin tetrachloride, tin tetrabromide), aluminum halides (e.g. aluminum chloride, aluminum bromide), and trihaloacetic acids (e.g. trichloroacetic acid, trifluoroacetic acid). This elimination reaction is preferably carried out in the presence of cation trapping agents (e.g. anisole, phenol) and is usually carried out in a solvent such as nitroalkane (e.g. nitromethane, nitroethane), alkylene halide (e.g. methylene chloride, ethylene chloride), diethyl ether, carbon disulfide or any other solvent which does not adversely influence the reaction. These solvents may be used alone or upon mixing with one another.

The reduction elimination can be preferably conducted for eliminating a protective group such as halo(lower)alkyl (e.g. 2-iodoethyl, 2,2,2-trichloroethyl) ester, and aryl(lower)alkyl (e.g. benzyl) ester.

The reduction applicable for the elimination reaction includes the reduction using a combination of a metal (e.g. zinc, zinc amalgam) or a salt of chromium compound (e.g. chromous chloride, chromous acetate) and an organic or inorganic acid (e.g. acetic acid, propionic acid, hydrochloric acid); and conventional catalytic reduction in the presence of a conventional metallic catalyst (e.g. palladium carbon, Raney nickel).

The reaction temperature is not critical and the reaction is usually carried out under cooling, at ambient temperature or under warming.

Process 3

The compound (I) or a salt thereof can be prepared by reacting the compound (IV) or its reactive derivative at the amino group or a salt thereof with the compound (V) or its reactive derivative at the carboxy group or a salt thereof.

Suitable reactive derivative at the carboxy group of the compound (V) includes an acid halide, an acid anhydride, an activated amide and an activated ester. Suitable examples of the reactive derivatives may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid), dialkylphosphorous acid, sulfurous acid, thiosulfuric acid, sulfuric acid, sulfonic acid (e.g. methanesulfonic acid), aliphatic carboxylic acid (e.g. acetic acid, propionic acid, butyric acid, isobutyric acid, pivalic acid, pentanoic acid, isopentanoic acid, 2-ethylbutyric acid, trichloroacetic acid), or aromatic carboxylic acid (e.g. benzoic acid); a symmetrical acid anhydride; an activated amide with imidazole, 4-substituted imidazole, dimethylpyrazole, triazole or tetrazole; an activated ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester) or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-1H-benzotriazole). These reactive derivatives can optionally be selected from them according to the kind of the compound (V) to be used.

Suitable salts of the compound (V) and its reactive derivative include a base salt such as an alkali metal salt (e.g. sodium salt, potassium salt), an alkaline earth metal salt (e.g. calcium salt, magnesium salt), an ammonium salt and an organic base salt (e.g. trimethylamine salt, triethylamine salt, pyridine salt, picoline salt, dicyclohexylamine salt, N,N'-dibenzylethylenediamine salt).

Suitable reactive derivative at the amino group of the compound (IV) includes Schiff's base type imino or its tautomeric enamine type isomer formed by the reaction of the compound (IV) with a carbonyl compound such as aldehyde or ketone; a silyl derivative formed by the reaction of the compound (IV) with a silyl compound such as bis(trimethylsilyl)acetamide, mono(trimethylsilyl) acetamide or bis(trimethylsilyl)acetamide, mono (trimethylsilyl)acetamide or bis(trimethylsilyl)urea; and a derivative formed by reaction of the compound (IV) with phosphorus trichloride or phosgene.

The reaction is usually carried out in a solvent such as water, an alcohol (e.g. methanol, ethanol), acetone, dioxane, acetonitrile, chloroform, methylene chloride, ethylene chloride, tetrahydrofuran, ethyl acetate, N,N-dimethylformamide, pyridine or any other solvent which does not adversely influence the reaction. These conventional solvent may also be used in a mixture with water.

In this reaction, when the compound (V) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate (e.g. ethyl chloroformate, isopropyl chloroformate); triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; or so-called Vilsmeier reagent prepared by the reaction of N,N-dimethylformamide with thionyl chloride, phosgene, trichloromethyl chloroformate, phosphorus oxychloride or oxalyl chloride.

The reaction may also be carried out in the presence of an inorganic or organic base such as an alkali metal hydrogencarbonate, tri(lower)alkylamine, pyridine, N-(lower)alkylmorpholine or N,N-di(lower) alkylbenzylamine.

The reaction temperature is not critical and the reaction is usually carried out under cooling to warming.

Process 4

The object compound (Ia) or a salt thereof can be prepared by subjecting the compound (Ib) or a salt thereof to protecting reaction of carboxy.

This reaction can be carried out according to a conventional manner such as the ones described in Examples or the similar manners thereto.

The processes for preparing the starting compounds (II) and (IV) or a salt thereof are explained in detail in the following.

Process A

The compound (VII) or a salt thereof can be prepared by subjecting the compound (VI) or a salt thereof to elimination of amino protective group in the presence of an acid.

Suitable acid includes an organic acid (e.g. formic acid, acetic acid, propionic acid) and an inorganic acid (e.g. hydrochloric acid, hydrobromic acid, sulfuric acid).

The reaction is usually carried out in a solvent such as water, an alcohol (e.g. methanol, ethanol), methylene chloride, chloroform, tetrachloromethane, tetrahydrofuran, a mixture thereof or any other solvent which does not adversely influence the reaction.

The reaction temperature is not critical and the reaction is usually carried out under cooling to heating.

Process B

The compound (II) or a salt thereof can be prepared by reacting the compound (VII) or its reactive derivative at the amino group or a salt thereof with the compound (V) or its reactive derivative at the carboxy group or a salt thereof.

This reaction can be carried out in substantially the same manner as in Process 3, and therefore the reaction mode and reaction conditions (e.g. reactive derivatives, condensing agents, solvent, reaction temperature) of this reaction are to be referred to those as explained in Process 3.

Process C

The compound (VIII) or a salt thereof can be prepared by reacting the compound (VI) or a salt thereof with the compound (III) or a salt thereof.

This reaction can be carried out in substantially the same manner as in Process 1, and therefore the reaction mode and reaction conditions (e.g. bases, solvent, reaction temperature) of this reaction are to be referred to those as explained in Process 1.

Process D

The compound (IV) or a salt thereof can be prepared by subjecting the compound (VIII) or a salt thereof to elimination of the amino protective group in the presence of an acid.

This reaction can be carried out in substantially the same manner as in Process A, and therefore the reaction mode and reaction conditions (e.g. acids, solvent, reaction temperature) of this reaction are to be referred to those as explained in Process A.

The starting compound (VI) can be prepared by the known method such as disclosed in Japanese Patent Publication No. 52-83492.

The compounds obtained by the above processes can be isolated and purified by a conventional method such as pulverization, recrystallization, column chromatography or reprecipitation.

It is to be noted that each of the object compound (I) may include one or more stereoisomer such as optical isomer(s) and geometrical isomer(s) due to asymmetric carbon atom(s) or double bond(s) and all such isomers and mixture thereof are included within the scope of this invention.

The cephem compound (I) and a pharmaceutically acceptable salt thereof include a solvate [e.g., enclosure compound (e.g., hydrate, etc.)].

The cephem compound (I) and a pharmaceutically acceptable salt thereof include both their crystal form and non-crystal form.

The cephem compound (I) and a pharmaceutically acceptable salt thereof are stable even in a strong acid such as gastric juice.

The cephem compound (I) and a pharmaceutically acceptable salt thereof possess antimicrobial activity against $H.$ $pylori$, and are useful for the prophylaxis and/or treatment of gastritis, ulcer (e.g. gastric ulcer, duodenal ulcer, anastomotic ulcer), MALT lymphoma and non-ulcer dyspepsia and the prophylaxis of stomach cancer. The cephem compound (I) and a pharmaceutically acceptable salt thereof may be administered in combination with an acid secretion inhibitor such as an $H_2$-blocker (e.g. cimetidine, ranitidine, famotidine, etc.) or a proton pump inhibitor (e.g. omeprazole, lansoprazole, etc.) for the prophylaxis and/or treatment of chronic gastritis, peptic ulcer (e.g. gastric ulcer, duodenal ulcer, anastomotic ulcer), MALT lymphoma and non-ulcer dyspepsia and the prophylaxis of stomach cancer.

The cephem compound (I) and a pharmaceutically acceptable salt thereof are particularly effective for the prophylaxis and/or treatment of the diseases caused by $Helicobacter$ $pylori$ infection such as gastritis, ulcer [e.g. peptic ulcer (e.g. gastric ulcer, duodenal ulcer, anomatic ulcer, etc.) etc.], MALT lymphoma, non-ulcer-dyspepsia and stomach cancer when administered with an acid secretion inhibitor such as an $H_2$-blocker (e.g. cimetidine, ranitidine, famotidine, etc.) or a proton pump inhibitor (e.g. omeprazole, lansoprazole, etc.).

Particularly, since the cephem compound (I) and a pharmaceutically acceptable salt thereof possess selective antimicrobial activity against $H.$ $pylori$, they can act selectively on $H.$ $pylori$ without exerting adverse influence on other useful enterobacteria. Accordingly, the cephem compound (I) and pharmaceutically acceptable salts thereof serve well for the eradication of $H.$ $pylori$ and are useful for the treatment of ulcers and/or prevention of recurrence of ulcers. The cephem compound (I) and a pharmaceutically acceptable salt thereof may be administered in combination with an acid secretion inhibitor such as an $H_2$-blocker (e.g. cimetidine, ranitidine, famotidine, etc.) or a proton pump inhibitor (e.g. omeprazole, lansoprazole, etc.) for the treatment of ulcers and/or prevention of recurrence of ulcers.

For therapeutic purpose, the compound (I) and a pharmaceutically acceptable salt thereof of the present invention can be used as they are, or in the form of pharmaceutical preparations containing one of said compounds as an active ingredient in admixture with a pharmaceutically acceptable carrier such as an organic or inorganic solid or liquid excipient suitable for oral or parenteral administration. The pharmaceutical preparations may be capsules, tablets, dragees, granules, solution, suspension or emulsion. If desired, there may be included, in these preparations, auxiliary substances, stabilizing agents, wetting or emulsifying agents, buffers and other commonly used additives such as lactose, sialic acid, magnesium stearate, terra alba, sucrose, corn starch, talc, gelatin, agar, pectin, peanut oil, olive oil, cacao butter and ethylene glycol.

While the dosage of the compound (I) will vary depending upon the age and condition of the patient, an average single dose of about 0.1 mg, 1 mg, 10 mg, 25 mg, 50 mg, 100 mg, 250 mg, 500 mg, 1000 mg and 2000 mg of the compound (I) may be effective for treating ulcer. In general, amounts between 0.1 mg/body and about 2,000 mg/body may be administered per day.

When the compound (I) is used in combination with an acid secretion inhibitor, a ratio by weight of the compound (I) to an acid secretion inhibitor is in the following range:

compound (I)/acid secretion inhibitor=0.01/1–100/1 A preferred range is compound (I)/acid secretion inhibitor=1/1–100/1 A more preferred range is compound (I)/acid secretion inhibitor=2.5/1–50/1
Another preferred range is
compound (I)/acid secretion inhibitor=0.1/1–10/1
According to the present invention, the followings are provided.
(1) A product comprising the cephem compound (I) and a pharmaceutically acceptable salt thereof and an acid secretion inhibitor as a combined preparation for simultaneous, separate or sequential use for the prevention and/or treatment of the diseases caused by *Helicobacter pylori* infection.
(2) The cephem compound (I) and a pharmaceutically acceptable salt thereof for adjuvant therapy of the diseases caused by *Helicobacter pylori* infection, with an acid secretion inhibitor.
(3) Use of the cephem compound (I) and a pharmaceutically acceptable salt thereof and an acid secretion inhibitor for the manufacture of medicament for simultaneous, separate or sequential use for the prevention and/or treatment of the disease caused by *Helicobacter pylori* infection.
(4) A product comprising the cephem compound (I) and an acid secretion inhibitor for simultaneous, separate or sequential use as a medicament.
(5) A pharmaceutical composition, comprising the cephem compound (I) and an acid secretion inhibitor and optionally pharmaceutically acceptable carriers or excipients.
(6) A pharmaceutical composition, characterized in that the composition is adapted for only oral administration and comprises, as an active ingredient, the cephem compound (I) and a pharmaceutically acceptable salt thereof and an acid secretion inhibitor.
(7) A product comprising:
 a) the cephem compound (I) or a pharmaceutically acceptable salt thereof, and,
 b) an acid secretion inhibitor in a ratio by weight of: a) to b) of from 0.01/1 to 100/1.
(8) A method for treatment of inhibition of the diseases caused by *Helicobacter pylori* infection which comprises administering an effective amount of the cephem compound (I) to a patient in need of said treatment of inhibition.
(9) The method of the above (8) wherein the cephem compound (I) is administered to said patient in combination with an acid secretion inhibitor in a ratio by weight of the cephem compound (I) to an acid secretion inhibitor in the range of from 0.01/1 to 100/1.
(10) A method for the veterinary treatment of an animal infected with *Helicobacter pylori* which comprises administering an effective amount of the cephem compound (I) to an animal in need of said treatment.
(11) The method of the above (10) wherein the cephem compound (I) is administered to said animal in combination with an acid secretion inhibitor in a ratio by weight of the cephem compound (I) to an acid secretion inhibitor in the range of from 0.01/1 to 100/1.

In order to illustrate the usefulness of the object compound (I), the pharmacological test data of the representative compound of the compound (I) are shown in the following.

Test 1 (Anti-Microbial Activity Against *Helicobacter pylori*)

Test Method

In vitro anti-microbial activity against *Helicobacter pylori* and determined by the two-fold agar plate dilution method as described below.

*Helicobacter pylori* was cultured on a Brucella agar plate containing 3% horse serum and 2% starch at 37° C. for 3 days under 10% $CO_2$, and suspended in a Brucella broth to a turbidity of McFarland No. 1. This suspension was inoculated on Brucella agar supplemented with 7% horse blood containing graded concentrations of the test compound, and the minimum inhibitory concentration (MIC) was expressed in terms of µg/ml after incubation at 37° C. for 3 days under 10% $CO_2$.

Test Compound

7β-(2-Phenylacetamido)-3-(5-aminomethyl-1,3,4-thiadiazol-2-yl)thio-3-cephem-4-carboxylic acid trifluoroacetic acid salt Test Result

| MIC (µg/ml) | |
|---|---|
| Test strain | Test Compound |
| *H. pylori* FP 1757 | <0.02 |

Test 2 (Therapeutic Effects in Mouse Model)

Test Method 1.5 ml of approx. $10^8$ cfu/ml of *H. pylori* FP 1757 was orally infected into 4 weeks old male ICR mice (Nippon SLC, Hamamatsu, Japan) which had been fasted overnight. Four days after infection, the test compound was orally administered to the mice at the dose of 0.32 mg/kg/time twice per day, for 4 days. The test compound was suspended in 0.5% methylcellulose and administered to the mice. The mice were sacrificed at 2 weeks after the final administration and the gastric mucosa was scraped and homogenized in 1 ml of 0.1 M phosphate buffered saline. 0.1 ml aliquots were inoculated onto Brucella agar plate containing 3% horse serum, 2% starch and antibiotics. All plates were incubated at 37° C. under 10% $CO_2$ for 4 or 5 days. Colonies grown on the plate were counted, and the therapeutic effect was evaluated.

Test Compound

7β-[2-(2-Thienyl)acetamido]-3-(4-carboxymethylthiazol-2-yl)thio-3-cephem-4-carboxylic acid (the compound of Example 72).

Test Result

| | dose (mg/kg/time) | eradication (%) |
|---|---|---|
| Test Compound | 0.32 | >80% |

Test 3 (Subacute Toxicity)

Test Method

The test compound suspended in 0.5% methylcellulose was orally administered to male rats at a dose of 100 or 32 mg/kg/day for 2 weeks.

Test Compound

7β-(2-Phenylacetamido)-3-(4-carbamoylmethylthiazol-2-yl)thio-3-cephem-4-carboxylic acid (the compound of Example 14).

Test Result

| Test Compound | non toxicological dose (mg/kg/day) |
|---|---|
| Test Compound | 100 |

The following Preparations and Examples are given for the purpose of illustrating the present invention in more detail.

Preparation 1

To a solution of ethyl 2-mercapto-4-thiazole acetate (203 mg) in 1,4-dioxane (1.0 ml) was added 1N-sodium hydroxide solution (2.0 ml) at room temperature. After stirring at the same temperature for 2 hours, the solution was poured into a mixture of ethyl acetate and water, and adjusted to pH 8.0 with 1N-hydrochloric acid. The separated aqueous solution was adjusted to pH 3.0 with 1N-hydrochloric acid and extracted with ethyl acetate. The organic layer was washed with saturated sodium chloride solution, dried over magnesium sulfate and evaporated under reduced pressure to give 2-mercapto-4-thiazole acetic acid (120 mg).

NMR (DMSO-$d_6$, δ): 3.31 (1H, br s), 3.54 (2H, s), 6.72 (1H, s), 12.8 (1H, br s).

Preparation 2

To a mixture of ethyl 2-mercapto-4-thiazole acetate (203 mg) in ammonia solution (25%) (1.0 ml) was added ammonium chloride (5.3 mg) at room temperature. After stirring at the same temperature for 8 hours, the solution was poured into a mixture of tetrahydrofuran and saturated sodium chloride solution, and adjusted to pH 3.0 with 1N-hydrochloric acid and extracted with tetrahydrofuran twice. The combined organic layer was washed with saturated sodium chloride solution, dried over magnesium sulfate and evaporated under reduced pressure to give 2-mercapto-4-thiazole acetamide (171 mg).

NMR (DMSO-$d_6$, δ): 3.36 (2H, s), 6.65 (1H, s), 7.08 (1H, br s), 7.47 (1H, br s), 13.07 (1H, br s).

APCI-MASS (m/z): 175 (M+H)$^+$

Preparation 3

To a mixture of sodium hydride (24 mg) and N,N-dimethylformamide (4.0 ml) was added a solution of dimethylamine (54 mg) in tetrahydrofuran (320 μl) at −10° C. After stirring at room temperature for 1 hour, ethyl 2-mercapto-4-thiazole acetate (203 mg) was added to the mixture at room temperature. After stirring at room temperature for 3 hours, the mixture was poured into a mixture of water and ethyl acetate. The organic layer was washed with saturated sodium chloride solution, dried over magnesium sulfate and evaporated under reduced pressure. The residue was subjected to column chromatography on silica gel (eluent: ethyl acetate) to give N,N-dimethyl-2-mercapto-4-thiazole acetamide (72 mg).

NMR (DMSO-$d_6$, δ): 2.84 (3H, s), 3.00 (3H, s), 3.62 (2H, s), 6.63 (1H, s), 13.0 (1H, br s).

APCI-MASS (m/z): 203 (M+H)$^+$

Preparation 4

To a solution of ethyl 2-mercapto-4-methyl-5-thiazole acetate (217 mg) in tetrahydrofuran (5.0 ml) was added lithium aluminum hydride (38 mg) at ice-cooling. After stirring at 60° C. for 2 hours, the mixture was poured into a mixture of tetrahydrofuran and water, and adjusted to pH 3.0 with 1N-hydrochloric acid. The separated organic layer was washed with saturated aqueous sodium chloride solution, dried over magnesium sulfate and evaporated under reduced pressure. The residue was subjected to column chromatography on silica gel (eluent: hexane/ethyl acetate=2/3) to give 5-(2-hydroxyethyl)-2-mercapto-4-methylthiazole (89 mg).

NMR (DMSO-$d_6$, δ): 2.05 (3H, s), 2.59 (2H, t, J=6.1 Hz), 3.48 (2H, dt, J=6.1 and 5.2 Hz), 4.84 (1H, t, J=5.2 Hz), 12.9 (1H, br s).

APCI-MASS (m/z): 176 (M+H)$^+$

Preparation 5

4-(2-Hydroxyethyl)-2-mercaptothiazole was obtained according to a similar manner to that of Preparation 4.

NMR (DMSO-$d_6$, δ): 2.59 (2H, t, J=5.9 Hz), 3.61 (2H, dt, J=6.3 and 5.2 Hz), 4.77 (1H, t, J=5.2 Hz), 6.59 (1H, s), 13.1 (1H, br s).

APCI-MASS (m/z): 162 (M+H)$^+$

The following compounds (Preparations 6 and 7) were obtained according to a similar manner to that of Preparation 1.

Preparation 6

4-(2-Carboxyethyl)-2-mercaptothiazole

NMR (DMSO-$d_6$, δ): 2.5–2.8 (4H, m), 6.58 (1H, s), 12.27 (1H, br s), 13.13 (1H, br s).

Preparation 7

4-(Carboxymethyl)-2-metcapto-4,5,6,7-tetrahydrobenzothiazole

NMR (DMSO-$d_6$, δ): 1.4–2.1 (4H, m), 2.3–2.6 (3H, m), 2.7–2.9 (1H, m), 2.8–3.1 (1H, m), 12.87 (1H, br s).

APCI-MASS (m/z): 230 (M+H)$^+$

Preparation 8

The following compound was obtained according to a similar manner to that of Preparation 2.

4-(2-Carbamoylethyl)-2-mercaptothiazole

NMR (DMSO-$d_6$, δ): 2.3–2.6 (2H, m), 2.66 (2H, t, J=7.2 Hz), 6.51 (1H, s), 6.87 (1H, br s), 7.36 (1H, br s), 13.11 (1H, br s).

Preparation 9

To a solution of ammonium dithiocarbamate

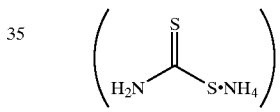

(1.10 g) in water (10 ml) were added ethyl bromopyruvate (1.95 g) and ethanol (5 ml) at ice-cooling. After stirring at room temperature for 1 hour, the mixture was poured into a mixture of water and ethyl acetate. The separated organic layer was washed with saturated sodium chloride solution (×2), dried over magnesium sulfate and evaporated under reduced pressure. The residue was subjected to column chromatography on silica gel (eluent: ethyl acetate/n-hexane) to give 4-ethoxycarbonyl-2-mercaptothiazole (1.21 g).

NMR (DMSO-$d_6$, δ): 1.25 (3H, t, J=7.1 Hz), 4.20 (2H, q, J=7.1 Hz), 10.97 (1H, s).

APCI-MASS (m/z): 190 (M+H)$^+$

Preparation 10

The following compound was obtained according to a similar manner to that of Prepration 9.

4-Ethoxycarbonylmethyl-2-mercapto-4,5,6,7-tetrahydrobenzothiazole

NMR (DMSO-$d_6$, δ): 1.1–1.3 (3H, m), 1.4–2.0 (4H, m), 2.3–2.6 (3H, m), 2.7–2.9 (1H, m), 2.9–3.1 (1H, m), 4.0–4.2 (2H, m), 12.9 (1H, m).

APCI-MASS (m/z): 258 (M+H)$^+$

Preparation 11

To a mixture of 4-ethoxycarbonyl-2-mercaptothiazole (150 mg) in ammonia solution (25%) (0.8 ml) was added ammonium chloride (4.2 mg) at room temperature. After stirring at the same temperature for 8 hours, the solution was poured into a mixture of tetrahydrofuran and saturated sodium chloride solution, and adjusted to pH 3.0 with 1N-hydrochloric acid. The separated tetrahydrofuran solution was washed with saturated sodium chloride solution, dried over magnesium sulfate and evaporated under reduced pressure. The residue was subjected to column chromatography on silica gel (eluent: chloroform/methanol) to give 4-carbamoyl-2-mercaptothiazole (70 mg).

NMR (DMSO-$d_6$, δ): 7.40 (1H, s), 7.45 (1H, br s), 7.62 (1H, br s).

APCI-MASS (m/z): 161 (M+H)$^+$

Preparation 12

To a solution of levulinic acid (19.0 g) in methanol (328 ml) was added bromine (26.2 g) at room temperature. After stirring at room temperature for 4 hours and reflux for 1 hour, the methanol was evaporated and the residue was poured into a mixture of water and ethyl acetate. The organic layer was washed with water, aqueous sodium hydrogen carbonate and saturated sodium chloride solution, and dried over magnesium sulfate and evaporated under reduced pressure. The residue was distilled (70–75° C./1 mmHg) to give methyl 5-bromolevulinate (15.0 g).

NMR (CDCl$_3$, δ): 2.66 (2H, t, J=6.1 Hz), 2.96 (2H, t, J=6.1 Hz), 3.69 (3H, s), 3.96 (2H, s).

Preparation 13

To a mixture of methyl 5-bromolevulinate (1.22 g), water (5.2 ml) and ethanol (2.6 ml) was added ammonium dithiocarbamate (642 mg) at room temperature. After stirring at room temperature for 2 hours, the resulting crystal was collected by filtration and washed with a cold mixture of water and ethanol at first and diisopropyl ether (×2) to give 4-(2-methoxycarbonylethyl)-2-mercaptothiazole (0.61 g).

NMR (DMSO-$d_6$, δ): 2.6–2.8 (4H, m), 3.60 (3H, s), 6.59 (1H, s), 13.15 (1H, br s).

APCI-MASS (m/z): 204 (M+H)$^+$

Preparation 14

To a solution of 2-formamido-4-carboxymethylthiazole (2.0 g) in tetrahydrofuran (20 ml) was added N-chlorosuccinimide (1.58 g) and stirred at room temperature overnight. The reaction mixture was added N-chlorosuccinimide (0.5 g) and stirred at the same temperature overnight. The reaction mixture was evaporated under reduced pressure and purified by column chromatography on silica gel (SiO$_2$=200 ml, chloroform:methanol:acetic acid=20:1:0.1) to give two fractions. The fraction 1 (upper spot by TLC) was purified by column chromatography on silica gel (SiO$_2$=200 ml, methanol:chloroform=2:8), then the elution was evaporated under reduced pressure. The residue was dissolved in a mixture of water and ethyl acetate, adjusted to pH 8.7 with saturated sodium hydrogencarbonate, and washed with ethyl acetate (×2). The aqueous layer was adjusted to pH 3.0 with 1N-hydrochloric acid, extracted with ethyl acetate (×2), dried over magnesium sulfate, and evaporated under reduced pressure to give white solid which was precipitated from ethyl acetate and N-hexane to give 5-chloro-2-formamido-4-carboxymethylthiazole (694 mg, 29.3%) as a white powder.

On the other hand, the fraction 2 (lower spot by TLC) was evaporated under reduced pressure and precipitated from chloroform and methanol and isopropyl ether to give 5-chloro-2-formamidothiazol-4-yl-(R,S)-chloromethyl carboxylic acid (870 mg, 39.4%).

Upper Spot

NMR (DMSO-$d_6$, δ): 3.60 (2H, s), 8.51 (1H, s), 12.54 (1H, br s).

APCI-MASS (m/z): 221 (M+H)$^+$

Lower Spot

NMR (DMSO-$d_6$, δ): 5.28 (1H, s), 8.50 (1H, s).

APCI-MASS (m/z): 255 (M+H)$^+$

Preparation 15

To a mixture of 5-amino-2-mercaptothiazole (6.61 g) in water (34 ml) and acetic acid (17 ml) was added a solution of sodium cyanate (6.50 g) in water (55 ml) at 35° C. After stirring at the same temperature for 2 hours, the solution was poured into a mixture of water, tetrahydrofuran and ethyl acetate, and adjusted to pH 3.0 with 1N-hydrochloric acid. The separated organic layer was washed with saturated sodium chloride solution (×2), dried over magnesium sulfate and evaporated under reduced pressure. The residue was subjected to column chromatography on silica gel (eluent: ethyl acetate/n-hexane) to give 5-ureido-2-mercaptothiazole (577 mg).

NMR (DMSO-$d_6$, δ): 4.25 (2H, s), 7.45 (1H, s), 10.63 (1H, br s), 13.36 (1H, br s).

Preparation 16

To a mixture of 2-mercaptothiazol-4-yl-acetamide (174 mg) and tetrahydrofuran (10 ml) was added Lawesson's reagent (202 mg) at room temperature. After stirring at room temperature overnight, the solution was poured into a mixture of water and ethyl acetate. The organic layer was washed with saturated sodium chloride solution, dried over magnesium sulfate and evaporated under reduced pressure. The residue was subjected to column chromatography on silica gel (eluent: ethyl acetate) to give 2-mercaptothiazol-4-yl-thioacetamide (188 mg).

NMR (DMSO-$d_6$, δ): 3.73 (2H, s), 6.68 (1H, s), 9.33 (1H, br s), 9.69 (1H, br s), 13.11 (1H, br s).

APCI-MASS (m/z): 191 (M+H)$^+$

Preparation 17

To a solution of ethyl 2-cyclohexanone acetate (1.0 g) in dimethoxyethane (15 ml) was added bromine (911 mg) at ice-cooling. After stirring at room temperature for 1 hour, the solution was poured into a mixture of water and ethyl acetate. The separated organic layer was washed with aqueous sodium hydrogen sulfite, sodium hydrogen carbonate and saturated sodium chloride orderly, and dried over magnesium sulfate and evaporated under reduced pressure. The residue was subjected to column chromatography on silica gel (eluent: ethyl acetate/n-hexane) to give ethyl 2-bromo-6-cyclohexanone acetate (258 mg).

NMR (CDCl$_3$, δ): 1.2–1.3 (3H, m), 1.3–1.9 (2H, m), 2.0–2.4 (5H, m), 2.6–2.9 (1H, m), 3.6–3.9 (1H, m), 4.1–4.3 (2H, m), 4.3–4.5 (1H, m).

APCI-MASS (m/z): 263 (M+H)$^+$

Preparation 18

To a solution of benzhydryl 7β-(2-phenylacetamido)-3-trifluoromethanesulfonyloxy-3-cephem-4-carboxylate (9.0 g) in a mixture of dichloromethane (27 ml) and anisole (9 ml) was added trifluoroacetic acid (18 ml) under ice-cooling. The mixture was stirred at the same temperature for 1 hour. The reaction mixture was poured into diisopropyl ether (380 ml) The precipitate was collected by filtration and dried to give 7β-(2-phenylacetamido)-3-trifluoromethanesulfonyloxy-3-cephem-4-carboxylic acid (7.55 g).

NMR (DMSO-$d_6$, δ): 3.48 and 3.58 (2H, ABq, J=14 Hz), 3.83 and 4.00 (2H, ABq, J=18 Hz), 5.26 (1H, d, J=5 Hz), 5.81 (1H, dd, J=5 and 8 Hz), 7.1–7.4 (5H, m), 9.24 (1H, d, J=8 Hz).

Preparation 19

To a mixture of ethyl 4-(bromoacetyl)benzoate (2 g), water (15 ml) and ethanol (14 ml) was added ammonium dithiocarbamate (813 mg) under stirring at room temperature. The stirring was continued for 1 hour at the same temperature and the resulting crystal was collected by filtration. The crystal was added to a mixture of water (15 ml) and ethanol (15 ml), and the mixture was refluxed for 1.5 hours under stirring. The stirring was continued for 30 minutes at 10° C. to give crystal, which were collected by filtration and dried, to give ethyl 4-(2-mercaptothiazol-4-yl) benzoate (1.15 g).

IR (KBr): 1699, 1608, 1587, 1456, 1290 $cm^{-1}$

NMR (DMSO-$d_6$, δ): 1.34 (3H, t, J=7.1 Hz), 4.33 (2H, q, J=7.1 Hz), 7.53 (1H, s), 7.96 (4H, dd, J=8.6 and 20.6 Hz), 13.8 (1H, s).

APCI-MASS (m/z): 266 $(M+H)^+$

Preparation 20

The following compound was obtained according to a similar manner to that of Preparation 1.

4-(2-Mercaptothiazol-4-yl)benzoic acid

IR (KBr): 1685, 1608, 1556, 1477, 1403, 1249 $cm^{-1}$

NMR (DMSO-$d_6$, δ): 7.51 (1H, s), 7.94 (4H, dd, J=8.6 and 22.1 Hz), 13.77 (1H, s).

APCI-MASS (m/z): 238 $(M+H)^+$

EXAMPLE 1

To a solution of 2-mercapto-4-thiazole acetic acid (105 mg) in tetrahydrofuran (1.1 ml) and dimethoxyethane (1.1 ml) was added potassium t-butoxide (119 mg) at −10° C., and the solution was stirred at the same temperature for 20 minutes. On the other hand, a solution of benzhydryl 7β-(2-phenylacetamido)-3-methanesulfonyloxy-3-cephem-4-carboxylate (267 mg) in tetrahydrofuran (1.3 ml) and dimethoxyethane (1.3 ml) was added to the above solution at −15° C. After stirring at ice-cooling for 2 hours, the solution was poured into a mixture of water, ethyl acetate and tetrahydrofuran, and adjusted to pH 3.0 with 1N-hydrochloric acid. The separated organic layer was washed with saturated sodium chloride solution, dried over magnesium sulfate and evaporated under reduced pressure. The residue was subjected to column chromatography on silica gel (eluent: ethyl acetate/methanol=8/1) to give benzhydryl 7β-(2-phenylacetamido)-3-(4-carboxymethylthiazol-2-yl)thio-3-cephem-4-carboxylate potassium salt (108 mg).

NMR (DMSO-$d_6$, δ): 3.4–3.8 (6H, m), 5.16 (1H, d, J=3.9 Hz), 5.52 (1H, dd, J=3.9 and 7.7 Hz), 6.87 (1H, s), 7.2–7.5 (15H, m), 7.61 (1H, s), 9.32 (1H, d, J=7.7 Hz).

FAB-MASS (m/z): 696 $(M+H)^+$

The following compounds (Example 2 to 9) were obtained according to a similar manner to that of Example 1.

EXAMPLE 2

Benzhydryl 7β-(2-phenylacetamido)-3-(4-carbamoylmethylthiazol-2-yl)thio-3-cephem-4-carboxylate NMR (DMSO-$d_6$, δ): 3.53 (2H, dd, J=13.9 and 17.3 Hz), 3.57 (2H, s), 3.54 and 3.76 (2H, ABq, J=17.7 Hz), 5.25 (1H, d, J=5.0 Hz), 5.82 (1H, dd, J=5.0 and 8.4 Hz), 6.97 (1H, s), 7.01 (1H, br s), 7.2–7.5 (16H, m), 7.56 (1H, s), 9.26 (1H, d, J=8.4 Hz).

APCI-MASS (m/z): 657 $(M+H)^+$

EXAMPLE 3

Benzhydryl 7β-(2-phenylacetamido)-3-(5-carboxymethyl-4-methylthiazol-2-yl)thio-3-cephem-4-carboxylate potassium salt NMR (DMSO-$d_6$, δ): 2.27 (3H, s), 3.4–3.9 (6H, m), 5.26 (1H, d, J=5.0 Hz), 5.82 (1H, dd, J=5.0 and 8.4 Hz), 6.96 (1H, s), 7.1–7.5 (15H, m), 9.26 (1H, d, J=8.4 Hz).

EXAMPLE 4

Benzhydryl 7β-(2-phenylacetamido)-3-(4-N,N-dimethyl-carbamoylmethylthiazol-2-yl)thio-3-cephem-4-carboxylate NMR (DMSO-$d_6$, δ): 2.83 (3H, s), 3.03 (3H, s), 3.53 (2H, d, J=3.8 Hz), 3.54 and 3.75 (2H, ABq, J=17.4 Hz), 3.84 (2H, s), 5.25 (1H, d, J=5.0 Hz), 5.81 (1H, dd, J=5.0 and 8.4 Hz), 6.97 (1H, s), 7.1–7.5 (15H, m), 7.55 (1H, s), 9.26 (1H, d, J=8.4 Hz).

EXAMPLE 5

Benzhydryl 7β-(2-phenylacetamido)-3-(5-hydroxymethyl-1,3,4-thiadiazol-2-yl)thio-3-cephem-4-carboxylate NMR (DMSO-$d_6$, δ): 3.52 (2H, d, J=4.1 Hz), 3.61 and 3.89 (2H, ABq, J=17.8 Hz), 4.84 (2H, s), 5.28 (1H, d, J=5.0 Hz), 5.87 (1H, dd, J=5.0 and 8.4 Hz), 6.30 (1H, br s), 6.98 (1H, s), 7.2–7.5 (15H, m), 9.30 (1H, d, J=8.4 Hz).

EXAMPLE 6

Benzhydryl 7β-[2-(3-thienyl)acetamido]-3-(5-hydroxymethyl-1,3,4-thiadiazol-2-yl)thio-3-cephem-4-carboxylate NMR (CDCl$_3$, δ): 3.44 and 3.70 (2H, ABq, J=17.9 Hz), 3.66 (2H, s), 4.98 (2H, s), 5.00 (1H, d, J=5.0 Hz), 5.88 (1H, dd, J=5.0 and 9.1 Hz), 6.76 (1H, d, J=9.1 Hz), 6.96 (1H s), 6.9–7.4 (14H, m).

EXAMPLE 7

Benzhydryl 7β-[2-(2-thienyl)acetamido]-3-(5-hydroxymethyl-1,3,4-thiadiazol-2-yl)thio-3-cephem-4-carboxylate NMR (CDCl$_3$, δ): 3.43 and 3.68 (2H, ABq, J=18.1 Hz), 3.85 (2H, s), 5.00 (2H, s), 5.01 (1H, d, J=5.1 Hz), 5.89 (1H, dd, J=5.1 and 9.1 Hz), 6.86 (1H, d, J=9.1 Hz), 6.9–7.0 (3H, m), 7.1–7.4 (12H, m).

EXAMPLE 8

Benzhydryl 7β-(2-phenylacetamido)-3-[4-(2-hydroxyethyl)thiazol-2-yl]thio-3-cephem-4-carboxylate NMR (DMSO-$d_6$, δ): 2.86 (2H, t, J=6.7 Hz), 3.4–3.9 (6H, m), 4.69 (1H, t, J=5.3 Hz), 5.26 (1H, d, J=5.0 Hz), 5.82 (1H, dd, J=5.0 and 8.4 Hz), 6.97 (1H, s), 7.2–7.5 (16H, m), 9.27 (1H, d, J=8.4 Hz).

EXAMPLE 9

Benzhydryl 7β-(2-phenylacetamido)-3-[5-(2-hydroxyethyl)-4-methylthiazol-2-yl]thio-3-cephem-4-carboxylate NMR (DMSO-$d_6$, δ): 2.29 (3H, s), 2.86 (2H, t, J=6.1 Hz), 3.4–3.8 (6H, m), 4.92 (1H, t, J=5.2 Hz), 5.25 (1H, d, J=4.9 Hz), 5.80 (1H, d, J=4.9 and 8.3 Hz), 6.95 (1H, s), 7.2–7.6 (15H, m), 9.25 (1H, d, J=8.4 Hz).

EXAMPLE 10

To a solution of 2-mercapto-4-methyl-5-thiazole acetamido (489 mg) in tetrahydrofuran (4.9 ml) and dimethoxyethane (4.9 ml) was added potassium t-butoxide (224 mg) at −10° C., and the solution was stirred at the room temperature for 20 minutes. On the other hand, a solution of benzhydryl 7β-(2-phenylacetamido)-3-methanesulfonyloxy-3-cephem-4-carboxylate (1.16 g) in tetrahydrofuran (5.8 ml) and dimethoxyethane (5.8 ml) was added to the above solution at −15° C. After stirring at ice-cooling for 2 hours, the solution was poured into a mixture of water and ethyl acetate. The resulting crystal was collected by filtration, washed with water and ethyl acetate to give benzhydryl 7β-(2-phenylacetamido)-3-(5-carbamoylmethyl-4-methylthiazol-2-yl)thio-3-cephem-4-carboxylate (355 mg). The ethyl acetate layer of the filtrate was washed with saturated sodium chloride solution, dried over magnesium sulfate and evaporated under reduced pressure. Ethyl acetate was added to the residue, and the resulting crystal was collected by filtration and washed with ethyl acetate to give a second crystal of object compound (494 mg).

NMR (DMSO-$d_6$, δ): 2.28 (3H, s), 3.52 (2H, d, J=3.2 Hz), 3.53 and 3.75 (2H, ABq, J=17.7 Hz), 3.62 (2H, s), 5.26 (1H, d, J=4.9 Hz), 5.81 (1H, dd, J=4.9 and 8.4 Hz), 6.96 (1H, s), 7.17 (1H, br s), 7.2–7.5 (15H, m), 7.64 (1H, br s), 9.28 (1H, d, J=8.4 Hz).

EXAMPLE 11

To a solution of (5-N,N-dimethylaminomethyl-2-mercapto-1,3,4-thiadiazole (364 mg) in a mixture of tetrahydrofuran (7 ml) and 1,2-dimethoxyethane (7 ml) was added potassium t-butoxide (194 mg) at ice-cooling temperature with stirring and the mixture was stirred at the same temperature for 30 minutes. A benzhydryl 7β-(2-phenylacetamido)-3-methanesulfonyloxy-3-cephem-4-carboxylate (1.0 g) was added to the obtained solution at the same temperature and the mixture was stirred at the same temperature for 4 hours. The reaction mixture was poured into a mixture of 1N-hydrochloric acid (1.64 ml), water (30 ml) and ethyl acetate (30 ml). The organic layer was washed with water and saturated aqueous sodium chloride, dried over magnesium sulfate and concentrated in vacuo. The residue was subjected to column chromatography on silica gel (eluent: ethyl acetate/n-hexane=3/1) to give benzhydryl 7β-(2-phenylacetamido)-3-(5-N,N-dimethylaminomethyl-1,3,4-thiadiazol-2-yl)thio-3-cephem-4-carboxylate (310 mg).

NMR (DMSO-$d_6$, δ): 2.23 (6H, s), 3.53 (2H, m), 3.63 and 3.93 (2H, ABq, J=18 Hz), 3.83 (2H, m), 5.28 (1H, d, J=5 Hz), 5.88 (1H, dd, J=5 and 8 Hz), 6.99 (1H, s), 7.2–7.4 (15H, m), 9.30 (1H, d, J=8 Hz).

EXAMPLE 12

To a solution of (5-tert-butoxycarbonylaminomethyl-2-mercapto-1,3,4-thiadiazole (580 mg) in a mixture of tetrahydrofuran (3 ml) and 1,2-dimethoxyethane (3 ml) was added potassium tert-butoxide (239 mg) at −9° C. with stirring and the mixture was stirred at the −9~−5° C. for 30 minutes. A solution of benzhydryl 7β-(2-phenylacetamido)-3-methanesulfonyloxy-3-cephem-4-carboxylate (1.23 g) in a mixture of tetrahydrofuran (6 ml) and 1,2-dimethoxyethane (6 ml) was added to the obtained solution at −8° C. and the mixture was stirred at −5~−0° C. for 3.5 hours. The reaction mixture was poured into a mixture of ice-water (50 ml) and ethyl acetate (50 ml). The organic layer was washed with saturated aqueous sodium chloride, dried over magnesium sulfate and concentrated in vacuo. The residue was triturated with diethyl ether to give benzhydryl 7β(2-phenylacetamido)-3-(5-tert-butoxycarbonylaminomethyl-1,3,4-thiadiazol-2-yl)thio-3-cephem-4-carboxylate (0.82 g).

NMR (DMSO-$d_6$, δ): 3.5 (2H, m), 3.57 and 3.89 (2H, ABq, J=18 Hz), 4.47 (2H, d, J=5 Hz), 5.27 (1H, d, J=5 Hz), 5.86 (1H, dd, J=5 and 8 Hz), 6.99 (1H, s), 7.2–7.4 (15H, m), 7.83 (1H, m), 9.28 (1H, d, J=8 Hz).

FAB-MASS (m/z): 730.2 (M$^+$)

EXAMPLE 13

To a mixture of benzhydryl 7β-(2-phenylacetamido)-3-(4-carboxymethylthiazol-2-yl)thio-3-cephem-4-carboxylate potassium salt (1.10 g), anisole (1.10 ml) and dichloromethane (3.30 ml) was added trifluoroacetic acid (2.20 ml) at 15° C. After stirring at room temperature for 1 hour, the solution was poured into diisopropyl ether. The resulting precipitate was collected by filtration, added to a mixture of tetrahydrofuran and water and adjusted to pH 7.2 with an aqueous sodium bicarbonate. The separated aqueous solution was adjusted to pH 3.0 with 1N-hydrochloric acid and extracted with tetrahydrofuran. The tetrahydrofuran solution was washed with saturated sodium chloride solution, dried over magnesium sulfate and evaporated under reduced pressure. Ethyl acetate was added to the residue and the resulting crystal was collected by filtration to give 7β-(2-phenylacetamido)-3-(4-carboxymethylthiazol-2-yl)thio-3-cephem-4-carboxylic acid (595 mg).

IR (KBr): 1776, 1710, 1654, 1537 cm$^{-1}$

NMR (DMSO-$d_6$, δ): 3.48 and 3.73 (2H, ABq, J=17.5 Hz), 3.52 (2H, dd, J=14 and 17.6 Hz), 3.74 (2H, s), 5.19 (1H, d, J=4.9 Hz), 5.73 (1H, dd, J=5.0 and 8.3 Hz), 7.1–7.4 (5H, m), 7.59 (1H, s), 9.19 (1H, d, J=8.3 Hz).

FAB-MASS (m/z): 492 (M+H)$^+$

The following compounds (Example 14 to 21) were obtained according to a similar manner to that of Example 13.

EXAMPLE 14

7β-(2-Phenylacetamido)-3-(4-carbamoylmethylthiazol-2-yl)thio-3-cephem-4-carboxylic acid IR (KBr): 3440, 3284, 1776, 1664, 1539, 1357 cm$^{-1}$ NMR (DMSO-$d_6$, δ): 3.52 (2H, dd, J=13.9 and 17.8 Hz), 3.55 (2H, s), 3.50 and 3.74 (2H, ABq, J=17.6 Hz), 5.20 (1H, d, J=4.9 Hz), 5.74 (1H, dd, J=4.9 and 8.4 Hz), 6.99 (1H, br s), 7.1–7.4 (5H, m), 7.43 (1H, br s), 7.53 (1H, s), 9.21 (1H, d, J=8.4 Hz).

FAB-MASS (m/z): 491 (M+H)$^+$

EXAMPLE 15

7β-(2-Phenylacetamido)-3-(5-carboxymethyl-4-methylthiazol-2-yl)thio-3-cephem-4-carboxylic acid IR (KBr): 1776, 1718, 1657, 1539, 1367 cm$^{-1}$ NMR (DMSO-$d_6$, δ): 2.26 (3H, s), 3.52 (2H, dd, J=13.8 and 17.7 Hz), 3.48 and 3.72 (2H, ABq, J=17.6 Hz), 3.83 (2H, s), 5.20 (1H, d, J=4.9 Hz), 5.73 (1H, dd, J=4.9 and 8.4 Hz), 7.1–7.4 (5H, m), 9.22 (1H, d, J=8.4 Hz).

FAB-MASS (m/z): 506 (M+H)$^+$

EXAMPLE 16

7β-(2-Phenylacetamido)-3-(4-N,N-dimethylcarbamoylmethylthiazol-2-yl)thio-3-cephem-4-carboxylic acid IR (KBr): 3286, 1776, 1655, 1541, 1365 cm$^{-1}$ NMR (DMSO-$d_6$, δ): 2.84 (3H, s), 3.04 (3H, s), 3.52 (2H, s), 3.48 and 3.73 (2H, ABq, J=17.6 Hz), 3.83 (2H, s), 5.19 (1H, d, J=4.9 Hz), 5.74 (1H, dd, J=4.9 and 8.3 Hz), 7.1–7.4 (5H, m), 7.52 (1H, s), 9.21 (1H, d, J=8.3 Hz).

FAB-MASS (m/z): 519 (M+H)$^+$

EXAMPLE 17

7β-(2-Phenylacetamido)-3-(5-hydroxymethyl-1,3,4-thiadiazol-2-yl)thio-3-cephem-4-carboxylic acid IR (KBr): 1784, 1662, 1533 cm$^{-1}$ NMR (DMSO-$d_6$, δ): 3.52 (2H, d, J=4.2 Hz), 3.55 and 3.87 (2H, ABq, J=17.7 Hz), 4.83 (2H, s), 5.23 (1H, d, J=5.0

Hz), 5.79 (1H, dd, J=5.0 and 8.4 Hz), 6.29 (1H, br s), 7.2–7.4 (5H, m), 9.24 (1H, d, J=8.4 Hz).

FAB-MASS (m/z): 465.0 (M+H)⁺

EXAMPLE 18

7β-[2-(3-Thienyl)acetamido]-3-(5-hydroxymethyl-1,3,4-thidiazol-2-yl)thio-3-cephem-4-carboxylic acid IR (KBr): 1776, 1689, 1652, 1537 cm⁻¹

NMR (DMSO-$d_6$, δ): 3.54 (2H, s), 3.56 and 3.88 (2H, ABq, J=17.6 Hz), 4.83 (2H, s), 5.24 (1H, d, J=5.0 Hz), 5.80 (1H, dd, J=5.0 and 8.4 Hz), 6.30 (1H, br s), 7.0–7.5 (3H, m), 9.21 (1H, d, J=8.4 Hz).

FAB-MASS (m/z): 470.9 (M+H)⁺

EXAMPLE 19

7β-[2-(2-Thienyl)acetamido]-3-(5-hydroxymethyl-1,3,4-thiadiazol-2-yl)thio-3-cephem-4-carboxylic acid IR (KBr): 1776, 1689, 1652, 1539 cm⁻¹

NMR (DMSO-$d_6$, δ): 3.56 and 3.88 (2H, ABq, J=17.7 Hz), 3.76 (2H, s), 4.83 (2H, s), 5.25 (1H, d, J=5.0 Hz), 5.80 (1H, dd, J=5.0 and 8.4 Hz), 6.30 (1H, br s), 6.9–7.0 (2H, m), 7.36 (1H, dd, J=1.6 and 4.9 Hz), 9.28 (1H, d, J=8.4 Hz).

FAB-MASS (m/z): 470.9 (M+H)⁺

EXAMPLE 20

7β-(2-Phenylacetamido]-3-[4-(2-hydroxyethyl)thiazol-2-yl]thio-3-cephem-4-carboxylic acid IR (KBr): 1776, 1699, 1656, 1539 cm⁻¹

NMR (DMSO-$d_6$, δ): 2.84 (2H, t, J=6.7 Hz), 3.3–3.8 (6H, m), 4.67 (1H, br s), 5.21 (1H, d, J=4.9 Hz), 5.75 (1H, dd, J=4.9 and 8.3 Hz), 7.1–7.4 (5H, m), 7.45 (1H, s), 9.22 (1H, d, J=8.3 Hz).

FAB-MASS (m/z): 477.9 (M+H)⁺

EXAMPLE 21

7β-(2-Phenylacetamido]-3-[5-(2-hydroxyethyl)-4-methylthiazol-2-yl]thio-3-cephem-4-carboxylic acid IR (KBr): 1778, 1655, 1541 cm⁻¹

NMR (DMSO-$d_6$, δ) 2.28 (3H, s), 2.86 (2H, t, J=6.1 Hz), 3.4–3.8 (6H, m), 4.91 (1H, br s), 5.19 (1H, d, J=4.9 Hz), 5.72 (1H, dd, J=4.9 and 8.4 Hz), 7.1–7.4 (5H, m), 9.21 (1H, d, J=8.4 Hz).

FAB-MASS (m/z): 492.1 (M+H)⁺

EXAMPLE 22

To a mixture of benzhydryl 7β-(2-phenylacetamido)-3-(5-carbamoylmethyl-4-methylthiazol-2-yl)thio-3-cephem-4-carboxylate (0.80 g), anisole (0.80 ml) and dichloromethane (2.40 ml) was added trifluoroacetic acid (1.60 ml) at 15° C. After stirring at room temperature for 1 hour, the solution was poured into diisopropyl ether. The resulting precipitate was collected by filtration, added to a mixture of tetrahydrofuran and water, and adjusted to pH 7.5 with an aqueous sodium bicarbonate. The separated aqueous solution was washed with ethyl acetate and adjusted to pH 3.0 with 1N-hydrochloric acid. The resulting crystal was collected by filtration and washed with water to give 7β-(2-phenylacetamido)-3-(5-carbamoylmethyl-4-methylthiazol-2-yl)thio-3-cephem-4-carboxylic acid (445 mg).

IR (KBr): 3423, 3298, 1778, 1660, 1540, 1365 cm⁻¹

NMR (DMSO-$d_6$, δ): 2.28 (3H, s), 3.52 (2H, dd, J=13.6 and 17.5 Hz), 3.48 and 3.71 (2H, ABq, J=17.5 Hz), 3.61 (2H, s), 5.20 (1H, d, J=4.9 Hz), 5.73 (1H, dd, J=4.9 and 8.4 Hz), 7.14 (1H, br s), 7.1–7.4 (5H, m), 7.62 (1H, br s), 9.24 (1H, d, J=8.4 Hz).

FAB-MASS (m/z): 505 (M+H)⁺

EXAMPLE 23

To a solution of benzhydryl 7β-(2-phenylacetamido)-3-(5-N,N-dimethylaminomethyl-1,3,4-thiadiazol-2-yl)thio-3-cephem-4-carboxylate (290 mg) in a mixture of dichloromethane (0.9 ml) and anisole (0.47 ml) was added trifluoroacetic acid (0.6 ml) under ice-cooling. The mixture was stirred at room temperature for one hour. The reaction mixture was poured into diisopropyl ether (30 ml) and the resulting precipitate was collected by filtration and dried in vacuo. The precipitate was dissolved in a mixture of aqueous sodium hydrogen carbonate (10 ml), tetrahydrofuran (10 ml) and ethyl acetate (20 ml). The mixture was adjusted to pH 2.0 with 1N-hydrochloric acid. The organic layer was washed with saturated aqueous sodium chloride, dried over magnesium sulfate and concentrated in vacuo. The residue was triturated with ethyl acetate to give 7β-(2-phenylacetamido)-3-(5-N,N-dimethylaminomethyl-1,3,4-thiadiazol-2-yl)thio-3-cephem-4-carboxylic acid (150 mg).

IR (Nujol): 3300–3200, 1770, 1720, 1660, 1530 cm⁻¹

NMR (DMSO-$d_6$, δ): 2.79 (6H, s), 3.4–3.6 (2H, m), 3.61 and 3.91 (2H, ABq, J=18 Hz), 4.78 (2H, br s), 5.24 (1H, d, J=5 Hz), 5.79 (1H, dd, J=5.and 8 Hz), 7.2–7.3 (5H, m), 9.26 (1H, d, J=8 Hz).

FAB-MASS (m/z): 492 (M⁺)

EXAMPLE 24

To a solution of benzhydryl 7β-(2-phenylacetamido)-3-(5-tert-butoxycarbonylaminomethyl-1,3,4-thiadiazol-2-yl)thio-3-cephem-4-carboxylate (683 mg) in a mixture of dichloromethane (2.1 ml) and anisole (0.7 ml) was added trifluoroacetic acid (1.4 ml) under ice-cooling. The mixture was stirred at the same temperature for 30 minutes and at room temperature for 3 hours. The reaction mixture was poured into diisopropyl ether (70 ml). The precipitate was collected by filtration and dried over to give 7β-(2-phenylacetamido)-3-(5-aminomethyl-1,3,4-thiadiazol-2-yl)thio-3-cephem-4-carboxylic acid trifluoroacetic acid salt (525 mg).

IR (Nujol): 1770, 1660, 1530, 1200 cm⁻¹

NMR (DMSO-$d_6$, δ): 3.4–3.6 (2H, m), 3.49 and 3.87 (2H, ABq, J=17 Hz), 4.56 (2H, s), 5.21 (1H, d, J=5 Hz), 5.76 (1H, dd, J=5 and 8 Hz), 7.27 (5H, m), 9.22 (1H, d, J=8 Hz).

FAB-MASS (m/z): 464.0 (M+H)⁺

The following compounds (Examples 25 to 27) were obtained according to a similar manner to that of Example 13.

EXAMPLE 25

7β-(2-Phenylacetamido)-3-[4-(2-methoxycarbonylethyl)thiazol-2-yl]thio-3-cephem-4-carboxylic acid IR (KBr): 1782, 1728, 1693, 1662, 1539 cm⁻¹

NMR (DMSO-$d_6$, δ): 2.70 (2H, t, J=7.1 Hz), 2.97 (2H, t, J=7.4 Hz), 3.52 (2H, d, J=3.6 Hz), 3.59 (3H, s), 3.47 and 3.73 (2H, ABq, J=17.5 Hz), 5.20 (1H, d, J=4.9 Hz), 5.73 (1H, dd, J=8.3 Hz), 7.2–7.4 (5H, m), 7.46 (1H, s), 9.18 (1H, d, J=8.3 Hz).

FAB MASS (m/z): 520 (M+H)⁺

EXAMPLE 26

7β-(2-Phenylacetamido)-3-[4-(2-carboxyethyl)thiazol-2-yl]thio-3-cephem-4-carboxylic acid IR (KBr): 1778, 1699, 1660, 1535 cm$^{-1}$ NMR (DMSO-d$_6$, δ): 2.61 (2H, t, J=7.3 Hz), 2.93 (2H, t, J=7.3 Hz), 3.52 (2H, d, J=4.3 Hz), 3.47 and 3.74 (2H, ABq, J=17.5 Hz), 5.20 (1H, d, J=4.9 Hz), 5.74 (1H, dd, J=4.9 and 8.3 Hz), 7.1–7.4 (5H, m), 7.44 (1H, s), 9.21 (1H, d, J=8.3 Hz).

FAB-MASS (m/z): 506 (M+H)$^+$

EXAMPLE 27

7β-(2-Phenylacetamido)-3-(5-ureidothiazol-2-yl)thio-3-cephem-4-carboxylic acid

IR (KBr): 1772, 1664, 1527 cm$^{-1}$

NMR (DMSO-d$_6$, δ): 3.52 (2H, d, J=4.1 Hz), 3.53 and 3.81 (2H, ABq, J=17.5 Hz), 4.30 (2H, s), 5.23 (1H, d, J=5.0 Hz), 5.75 (1H, dd, J=5.0 and 8.4 Hz), 7.1–7.4 (5H, m), 7.99 (1H, s), 9.21 (1H, d, J=8.4 Hz), 10.73 (1H, s).

FAB-MASS (m/z): 491 (M+H)$^+$

The following compounds (Examples 28 to 37) were obtained according to a similar manner to that of Example 22.

EXAMPLE 28

7β-(2-Phenylacetamido)-3-[4-(N-methylcarbamoylmethyl)thiazol-2-yl]thio-3-cephem-4-carboxylic acid IR (KBr): 1776, 1658, 1652, 1538 cm$^{-1}$ NMR (DMSO-d$_6$, δ): 2.59 (3H, d, J=4.6 Hz), 3.52 (2H, d, J=4.1 Hz), 3.56 (2H, s), 3.49 and 3.74 (2H, ABq, J=17.5 Hz), 5.20 (1H, d, J=4.9 Hz), 5.74 (1H, dd, J=4.9 and 8.3 Hz), 7.1–7.4 (5H, m), 7.52 (1H, s), 7.89 (1H, m), 9.20 (1H, d, J=8.3 Hz).

FAB-MASS (m/z): 505 (M+H)$^+$

EXAMPLE 29

7β-(2-Phenylacetamido)-3-(4-morpholinocarbonylmethylthiazol-2-yl)thio-3-cephem-4-carboxylate IR (KBr): 1776, 1683, 1654, 1540 cm$^{-1}$ NMR (DMSO-d$_6$, δ): 3.4–3.6 (10H, m), 3.48 and 3.73 (2H, ABq, J=17.5 Hz), 3.86 (2H, s), 5.19 (1H, d, J=4.9 Hz), 5.76 (1H, dd, J=4.9 and 8.3 Hz), 7.1–7.4 (5H, m), 7.54 (1H, s), 9.19 (1H, d, J=8.3 Hz).

FAB-MASS (m/z): 561(M+H)$^+$

EXAMPLE 30

7β-(2-Phenylacetamido)-3-[4-[N-(2-pyridylmethyl)carbamoylmethyl]thiazol-2-yl]thio-3-cephem-4-carboxylic acid IR (KBr): 1774, 1660, 1618, 1539 cm$^{-1}$ NMR (DMSO-d$_6$, δ): 3.52 (2H, d, J=3.8 Hz), 3.50 and 3.74 (2H, ABq, J=17.5 Hz), 3.70 (2H, s), 4.39 (2H, d, J=5.9 Hz), 5.17 (1H, d, J=4.9 Hz), 5.74 (1H, dd, J=4.9 and 8.3 Hz), 7.1–7.4 (7H, m), 7.58 (1H, s), 7.74 (1H, dt, J=1.8 and 7.7 Hz), 8.50 (1H, d, J=4.0 Hz), 8.61 (1H, t, J=6.0 Hz), 9.20 (1H, d, J=8.3 Hz).

FAB-MASS (m/z): 582 (M+H)$^+$

EXAMPLE 31

7β-(2-Phenylacetamido)-3-(4-carbamoylthiazol-2-yl)thio-3-cephem-4-carboxylic acid IR (KBr): 1780, 1662, 1581, 1537 cm$^{-1}$ NMR (DMSO-d$_6$, δ): 3.53 (2H, d, J=4.5 Hz), 3.60 and 3.93 (2H, ABq, J=17.6 Hz), 5.22 (1H, d, J=5.0 Hz), 5.78 (1H, dd, J=5.0 and 8.3 Hz), 7.2–7.4 (5H, m), 7.65 (1H, br s), 7.81 (1H, br s), 8.31 (1H, s), 9.23 (1H, d, J=8.3 Hz).

FAB-MASS (m/z): 477 (M+H)$^+$

EXAMPLE 32

7β-(2-Phenylacetamido)-3-[4-(2-carbamoylethyl)thiazol-2-yl]thio-3-cephem-4-carboxylic acid IR (KBr): 1774, 1683, 1660, 1531 cm$^{-1}$ NMR (DMSO-d$_6$, δ): 2.3–2.5 (2H, m), 2.90 (2H, t, J=7.7 Hz), 3.52 (2H, d, J=4.2 Hz), 3.46 and 3.73 (2H, ABq, J=17.5 Hz), 5.20 (1H, d, J=4.9 Hz), 5.74 (1H, dd, J=4.9 and 8.3 Hz), 6.77 (1H, br s), 7.1–7.3 (6H, m), 7.40 (1H, s), 9.19 (1H, d, J=8.3 Hz).

FAB-MASS (m/z): 505 (M+H)$^+$

EXAMPLE 33

7β-[2-(3-Thienyl)acetamido]-3-(4-carbamoylmethylthiazol-2-yl)thio-3-cephem-4-carboxylic acid IR (Nujol): 1760, 1660, 1530 cm$^{-1}$ NMR (DMSO-d$_6$, δ): 3.55 (2H, s), 3.55 (2H, s), 3.51 and 3.75 (2H, ABq, J=17.7 Hz), 5.20 (1H, d, J=4.9 Hz), 5.75 (1H, dd, J=4.9 and 8.3 Hz), 6.9–7.1 (2H, m), 7.25 (1H, m), 7.4–7.6 (3H, m), 9.18 (1H, d, J=8.3 Hz).

FAB-MASS (m/z): 497 (M+H)$^+$

EXAMPLE 34

7β-[2-(3-Thienyl)acetamido]-3-[4-(2-carboxyethyl)thiazol-2-yl]thio-3-cephem-4-carboxylic acid IR (Nujol): 1770, 1690, 1650, 1530 cm$^{-1}$ NMR (DMSO-d$_6$, δ): 2.61 (2H, t, J=7.3 Hz), 2.93 (2H, t, J=7.3 Hz), 3.54 (2H, s), 3.47 and 3.75 (2H, ABq, J=17.5 Hz), 5.21 (1H, d, J=4.9 Hz), 5.74 (1H, dd, J=4.9 and 8.3 Hz), 7.0–7.1 (1H, m), 7.2–7.3 (1H, m), 7.44 (1H, s), 7.4–7.5 (1H, m), 9.16 (1H, d, J=8.3 Hz).

FAB-MASS (m/z): 512 (M+H)$^+$

EXAMPLE 35

7β-[2-(2-Thienyl)acetamido]-3-(4-carbamoylmethylthiazol- 2-yl)thio-3-cephem-4-carboxylic acid IR (KBr): 1765, 1660, 1530 cm$^{-1}$ NMR (DMSO-d$_6$, δ): 3.55 (2H, s), 3.76 (2H, s), 3.48 and 3.75 (2H, ABq, J=17.5 Hz), 5.21 (1H, d, J=4.9 Hz), 5.75 (1H, dd, J=4.9 and 8.3 Hz), 6.9–7.0 (2H, m), 6.99 (1H, br s), 7.36 (1H, dd, J=1.5 and 4.8 Hz), 7.44 (1H, br s), 7.52 (1H, s), 9.24 (1H, d, J=8.3 Hz).

FAB-MASS (m/z): 497 (M+H)$^+$

EXAMPLE 36

7β-[2-(2-Thienyl)acetamido]-3-[4-(2-carboxyethyl)thiazol-2-yl]thio-3-cephem-4-carboxylic acid IR (Nujol): 1765, 1680, 1650, 1520 cm$^{-1}$ NMR (DMSO-d$_6$, δ): 2.61 (2H, t, J=7.4 Hz), 2.93 (2H, t, J=7.4 Hz), 3.5–3.9 (4H, m), 5.22 (1H, d, J=4.9 Hz), 5.75 (1H, dd, J=4.9 and 8.4 Hz), 6.8–7.0 (2H, m), 7.3–7.5 (2H, m), 9.23 (1H, d, J=8.4 Hz).

FAB-MASS (m/z): 512 (M+H)$^+$

EXAMPLE 37

7β-[2-(3-Thienyl)acetamido]-3-(4-carboxymethylthiazol-2-yl)thio-3-cephem-4-carboxylic acid IR (KBr): 1774, 1704, 1652, 1533 cm$^{-1}$ NMR (DMSO-d$_6$, δ): 3.54 (2H, s), 3.74 (2H, s), 3.47 and 3.75 (2H, ABq, J=17.7 Hz), 5.20 (1H, d, J=4.9 Hz), 5.75 (1H, dd, J=4.9 and 8.4 Hz), 7.0–7.1 (1H, m), 7.2–7.3 (1H, m), 7.4–7.5 (1H, m), 7.59 (1H, s), 9.19 (1H, d, J=8.4 Hz).

FAB-MASS (m/z): 498 (M+H)$^+$

EXAMPLE 38

To a solution of 4-carbamoyl-2-mercaptothiazole (450 mg) in tetrahydrofuran (27 ml) and dimethoxyethane (27 ml) was added potassium t-butoxide (242 mg) at −10° C., and the solution was stirred at the same temperature for 20 minutes. On the other hand, a solution of benzhydryl 7β-(2-phenylacetamido)-3-methanesulfonyloxy-3-cephem-4-carboxylate (1.25 g) in tetrahydrofuran (12.5 ml) and dimethoxyethane (12.5 ml) was added to the above solution at −15° C. After stirring at ice-cooling for 2 hours, the solution was poured into a mixture of water and ethyl acetate. The separated organic layer was washed with saturated sodium chloride solution, dried over magnesium sulfate and evaporated under reduced pressure. The residue was subjected to column chromatography on silica gel (eluent: ethyl acetate/n-hexane) to give benzhydryl 7β-(2-phenylacetamido)-3-(4-carbamoylthiazol-2-yl)thio-3-cephem-4-carboxylate (0.86 g).

NMR (DMSO-d$_6$, δ): 3.54 (2H, d, J=4.0 Hz), 3.66 and 3.94 (2H, ABq, J=17.6 Hz), 5.27 (1H, d, J=5.0 Hz), 5.86 (1H, dd, J=5.0 and 8.4 Hz), 6.98 (1H, s), 7.1–7.5 (15H, m), 7.64 (1H, br s), 7.78 (1H, br s), 8.32 (1H, s), 9.26 (1H, d, J=8.4 Hz).

APCI-MASS (m/z): 643 (M+H)$^+$

The following compounds (Examples 39 to 43) were obtained according to a similar manner to that of Example 38.

EXAMPLE 39

Potassium benzhydryl 7β-(2-phenylacetamido)-3-[4-(2-carboxyethyl)thiazol-2-yl]-thio-3-cephem-4-carboxylate NMR (DMSO-d$_6$, δ): 2.5–2.6 (2H, m), 2.8–3.0 (2H, m), 3.56 (2H, s), 3.52 and 3.77 (2H, ABq, J=17.3 Hz), 5.26 (1H, d, J=5.0 Hz), 5.82 (1H, dd, J=5.0 and 8.4 Hz), 6.96 (1H, s), 7.1–7.5 (16H, m), 9.24 (1H, d, J=8.4 Hz).

EXAMPLE 40

Benzhydryl 7β-(2-phenylacetamido)-3-(5-ureidothiazol-2-yl)thio-3-cephem-4-carboxylate NMR (DMSO-d$_6$, δ): 3.52 (2H, d, J=3.8 Hz), 3.57 and 3.85 (2H, ABq, J=17.7 Hz), 4.32 (2H, s), 5.28 (1H, d, J=5.0 Hz), 5.83 (1H, dd, J=5.0 and 8.4 Hz), 7.00 (1H, s), 7.1–7.5 (15H, m), 8.01 (1H, s), 9.25 (1H, d, J=8.4 Hz), 10.75 (1H, br s).

EXAMPLE 41

Benzhydryl 7β-(2-phenylacetamido)-3-(4-thiocarbamoylmethylthiazol-2-yl)thio-3-cephem-4-carboxylate NMR (DMSO-d$_6$, δ): 3.53 (2H, d, J=3.4 Hz), 3.54 and 3.76 (2H, ABq, J=17.9 Hz), 3.98 (2H, s), 5.24 (1H, d, J=5.0 Hz), 5.82 (1H, dd, J=5.0 and 8.4 Hz), 6.97 (1H, s), 7.2–7.5 (15H, m), 7.61 (1H, s), 9.26 (1H, d, J=8.4 Hz), 9.33 (1H, br s), 9.63 (1H, br s).

APCI-MASS (m/z): 673 (M+H)$^+$

EXAMPLE 42

Potassium benzhydryl 7β-[2-(2-thienyl)acetamido]-3-[4-(2-carboxyethyl)thiazol-2-yl]thio-3-cephem-4-carboxylate NMR (DMSO-d$_6$, δ) 2.5–2.7 (2H, m), 2.8–3.0 (2H, m), 3.5–3.8 (4H, m), 5.27 (1H, d, J=5.0 Hz), 5.83 (1H, dd, J=5.0 and 8.3 Hz), 6.9–7.0 (3H, m), 7.2–7.5 (12H, m), 9.28 (1H, d, J=8.3 Hz).

EXAMPLE 43

Potassium benzhydryl 7β-[2-(3-thienyl)acetamido]-3-(4-carboxymethylthiazol-2-yl)thio-3-cephem-4-carboxylate NMR (DMSO-d$_6$, δ): 3.54 (2H, s), 3.74 (2H, s), 3.52 and 3.75 (2H, ABq, J=17.3 Hz), 5.27 (1H, d, J=4.9 Hz), 5.83 (1H, dd, J=4.9 and 8.4 Hz), 6.9–7.1 (2H, m), 7.2–7.7 (13H, m), 9.23 (1H, d, J=8.4 Hz).

APCI-MASS (m/z): 664 (M+H)$^+$

EXAMPLE 44

To a mixture of benzhydryl 7β-(2-phenylacetamido)-3-(4-thiocarbamoylmethylthiazol-2-yl)thio-3-cephem-4-carboxylate (1.46 g), anisole (1.46 ml) and dichloromethane (4.38 ml) was added trifluoroacetic acid (2.92 ml) at 15° C. After stirring at room temperature for 1 hour, the solution was poured into diisopropyl ether. The resulting precipitate was collected by filtration, added to a mixture of tetrahydrofuran, ethyl acetate and water, and adjusted to pH 7.5 with an aqueous sodium hydrogen carbonate. The separated aqueous solution was washed with ethyl acetate, adjusted to pH 3.0 with 1N-hydrochloric acid and extracted with tetrahydrofuran. The tetrahydrofuran solution was washed with saturated sodium chloride solution, dried over magnesium sulfate and evaporated under reduced pressure. The residue was subjected to preparative HPLC (eluent: pH 3 buffer/acetonitrile) to give 7β-(2-phenylacetamido)-3-(4-thiocarbamoylmethylthiazol-2-yl)thio-3-cephem-4-carboxylic acid (62 mg).

IR (KBr): 1774, 1660, 1537 cm$^{-1}$

NMR (DMSO-d$_6$, δ): 3.52 (2H, d, J=3.9 Hz), 3.49 and 3.74 (2H, ABq, J=17.6 Hz), 3.97 (2H, s), 5.17 (1H, d, J=4.9 Hz), 5.73 (1H, dd, J=4.9 and 8.3 Hz), 7.1–7.4 (5H, m), 7.58 (1H, s), 9.21 (1H, d, J=8.3 Hz), 9.32 (1H, br s), 9.60 (1H, br s).

FAB-MASS (m/z): 507 (M+H)$^+$

The following compounds (Examples 45 and 46) were obtained according to a similar manner to that of Example 44.

EXAMPLE 45

7β-(2-Phenylacetamido)-3-(4-carboxymethyl-4,5,6,7-tetrahydrobenzothiazol-2-yl)thio-3-cephem-4-carboxylic acid [R,S either, polar]

IR (KBr): 1784, 1693, 1666, 1533 cm$^{-1}$

NMR (DMSO-d$_6$, δ): 1.3–2.1 (4H, m), 2.1–2.5 (1H, m), 2.6–2.9 (3H, m), 3.0–3.3 (1H, m), 3.52 (2H, d, J=4.1 Hz), 3.40 and 3.72 (2H, ABq, J=17.6 Hz), 5.19 (1H, d, J=4.9 Hz), 5.73 (1H, dd, J=4.9 and 8.3 Hz), 7.1–7.4 (5H, m), 9.19 (1H, d, J=8.3 Hz).

FAB-MASS (m/z): 546 (M+H)$^+$

EXAMPLE 46

7β-(2-Phenylacetamido)-3-(4-carboxymethyl-4,5,6,7-tetrahydrobenzothiazol-2-yl)thio-3-cephem-4-carboxylic acid [R,S either, less polar]

IR (KBr): 1781, 1712, 1670, 1533 cm$^{-1}$

NMR (DMSO-d$_6$, δ): 1.4–2.1 (4H, m), 2.1–2.5 (1H, m), 2.6–2.9 (3H, m), 3.0–3.3 (1H, m), 3.52 (2H, d, J=4.0 Hz), 3.40 and 3.75 (2H, ABq, J=17.6 Hz), 5.19 (1H, d, J=4.9 Hz), 5.73 (1H, dd, J=4.9 and 8.3 Hz), 7.1–7.4 (5H, m), 9.18 (1H, d, J=8.3 Hz).

FAB-MASS (m/z): 546 (M+H)$^+$

EXAMPLE 47

To a solution of 2-(2-mercaptothiazol-4-yl)acetamide (895 mg) in tetrahydrofuran (10.7 ml) and dimethoxyethane (10.7 ml) was added potassium t-butoxide (480 mg) at −10° C., and the solution was stirred at the same temperature for 20 minutes. On the other hand, a solution of benzhydryl 7β-[2-(3-thienyl)acetamido]-3-methanesulfonyloxy-3-cephem-4-carboxylate (2.5 g) in tetrahydrofuran (35 ml) was added to the above solution at −15° C. After stirring at ice-cooling for 2 hours, the solution was poured into a mixture of water and ethyl acetate. The separated organic layer was washed with saturated sodium chloride solution, dried over magnesium sulfate and evaporated under reduced pressure. Ethyl acetate was added to the residue and the resulting crystal was collected by filtration to give benzhydryl 7β-[2-(3-thienyl)acetamido]-3-(4-carbamoylmethylthiazol-2-yl)thio-3-cephem-4-carboxylate (1.64 g).

IR (KBr): 1784, 1666, 1537 cm$^{-1}$

NMR (DMSO-d$_6$, δ): 3.55 (2H, s), 3.57 (2H, s), 3.54 and 3.74 (2H, ABq, J=17.7 Hz), 5.26 (1H, d, J=5.0 Hz), 5.82 (1H, dd, J=5.0 and 8.4 Hz), 6.97 (1H, s), 7.0–7.1 (2H, m), 7.2–7.5 (13H, m), 7.56 (1H, s), 9.22 (1H, d, J=8.4 Hz).

APCI-MASS (m/z): 663 (M+H)$^+$

The following compounds (Examples 48 to 51) were obtained according to a similar manner to that of Example 47.

EXAMPLE 48

Benzhydryl 7β-(2-phenylacetamido)-3-(5-aminothiazol-2-yl)thio-3-cephem-4-carboxylate NMR (DMSO-d$_6$, δ): 3.45 (2H, s), 3.53 (2H, d, J=3.8 Hz), 5.20 (1H, d, J=4.7 Hz), 5.71 (1H, dd, J=4.7 and 8.3 Hz), 6.31 (2H, br s), 6.87 (1H, s), 6.93 (1H, s), 7.2–7.6 (15H, m), 9.13 (1H, d, J=8.3 Hz).

EXAMPLE 49

Benzhydryl 7β-(2-phenylacetamido)-3-[4-(2-carbamoylethyl)thiazol-2-yl]thio-3-cephem-4-carboxylate NMR (DMSO-d$_6$, δ) 2.4–2.5 (2H, m), 2.92 (2H, t, J=7.9 Hz), 3.53 (2H, d, J=3.3 Hz), 3.52 and 3.76 (2H, ABq, J=17.7 Hz), 5.26 (1H, d, J=5.0 Hz), 5.82 (1H, dd, J=5.0 and 8.4 Hz), 6.78 (1H, br s), 6.97 (1H, s), 7.2–7.5 (17H, m), 9.24 (1H, d, J=8.4 Hz).

EXAMPLE 50

Benzhydryl 7β-(2-phenylacetamido)-3-[4-(2-methoxycarbonylethyl)thiazol-2-yl]thio-3-cephem-4-carboxylate NMR (DMSO-d$_6$, δ): 2.71 (2H, t, J=7.3 Hz), 2.97 (2H, t, J=7.3 Hz), 3.53 (2H, d, J=3.6 Hz), 3.58 (3H, s), 3.54 and 3.76 (2H, ABq, J=17.7 Hz), 5.26 (1H, d, J=4.9 Hz), 5.82 (1H, dd, J=4.9 and 8.4 Hz), 6.96 (1H, s), 7.1–7.5 (15H, m), 7.48 (1H, s), 9.24 (1H, d, J=8.4 Hz).

EXAMPLE 51

Benzhydryl 7β-[2-(2-thienyl)acetamido]-3-(4-carbamoylmethylthiazol-2-yl)thio-3-cephem-4-carboxylate IR (KBr): 1780, 1666, 1537 cm$^{-1}$ NMR (DMSO-d$_6$, δ): 3.57 (2H, s), 3.76 (2H, s), 3.52 and 3.78 (2H, ABq, J=17.5 Hz), 5.27 (1H, d, J=5.0 Hz), 5.83 (1H, dd, J=5.0 and 8.3 Hz), 6.9–7.1 (4H, m), 7.2–7.5 (12H, m), 7.55 (1H, s), 9.28 (1H, d, J=8.3 Hz).

APCI-MASS (m/z): 663 (M+H)$^+$

EXAMPLE 52

Phosphorus oxychloride (473 μl) was added dropwise to a mixture of N,N-dimethylformamide (388 μl) and ethyl acetate (1 ml) under ice-cooling. After being stirred for 10 minutes at the same temperature, the mixture was cooled until a precipitate appeared. To the suspension was added tetrahydrofuran (17 ml). The suspension was stirred at the same temperature for 30 minutes. To the suspension was added 2-(5-tert-butoxycarbonylamino-1,2,4-thiadiazol-3-yl)acetic acid (1.0 g). The mixture was stirred at the same temperature for 30 minutes to give an activated acid solution. On the other hand, to a suspension of 7β-amino-3-(5-methyl-1,3,4-thiadiazol-2-yl)thio-3-cephem-4-carboxylic acid (1.16 g) in tetrahydrofuran (17 ml) was added N-trimethylsilylacetamide (3.7 g). The suspension was stirred at 20–40° C. for 40 minutes to give a clear solution. To the solution was added the activated acid solution prepared above at −20° C. The mixture was stirred at −20~5° C. for 40 minutes. The reaction mixture was added to a mixture of ethyl acetate (100 ml), sodium hydrogen carbonate (1.59 g) and water (100 ml). To the separated aqueous solution was added ethyl acetate (100 ml). The mixture was adjusted to pH 2 with 1 N-hydrochloric acid. The organic layer was washed with saturated aqueous sodium chloride, dried over magnesium sulfate and concentrated in vacuo. The residue was triturated with diethyl ether to give 7β-[2-(5-tert-butoxycarbonylamino-1,2,4-thiadiazol-3-yl)acetamido]-3-(5-methyl-1,3,4-thiadiazol-2-yl)thio-3-cephem-4-carboxylic acid (1.17 g).

NMR (DMSO-d$_6$, δ): 1.50 (9H, s), 2.72 (3H, s), 3.54 and 3.86 (2H, ABq, J=17 Hz), 3.70 and 3.79 (2H, ABq, J=15 Hz), 5.24 (1H, d, J=5 Hz), 5.80 (1H, dd, J=5 and 8 Hz), 9.22 (1H, d, J=8 Hz), 12.29 (1H, br s).

FAB-MASS (m/z): 572.0

The following compounds (Examples 53 to 56) were obtained according to a similar manner to that of Example 52.

EXAMPLE 53

7β-[2-(5-Chloro-2-formylaminothiazol-4-yl)acetamido]-3-(5-methyl-1,3,4-thiadiazol-2-yl)thio-3-cephem-4-carboxylic acid NMR (DMSO-d$_6$, δ): 2.72 (3H, s), 3.54 and 3.85 (2H, ABq, J=17 Hz), 3.60 (2H, s), 5.23 (1H, d, J=5 Hz), 5.79 (1H, dd, J=5 Hz and 8 Hz), 8.49 (1H, s), 9.20 (1H, d, J=8 Hz), 12.52 (1H, br s).

EXAMPLE 54

7β-(1-Phenyl-1-cyclopropanecarboxamido)-3-(5-methyl-1,3,4-thiadiazol-2-yl)thio-3-cephem-4-carboxylic acid NMR (DMSO-$d_6$, δ): 1.0–1.2 (2H, m), 1.3–1.5 (2H, m), 2.72 (3H, s), 3.51 and 3.79 (2H, ABq, J=17 Hz), 5.18 (1H, d, J=5 Hz), 5.68 (1H, dd, J=5 and 8 Hz), 7.2–7.4 (5H, m), 7.74 (1H, d, J=8 Hz).

FAB-MASS (m/z): 475.1

EXAMPLE 55

7β-[(Z)-2-(2-t-Butoxycarbonylaminothiazol-4-yl)-2-pentenoylamino]-3-(5-methyl-1,3,4-thiadiazol-2-yl)thio-3-cephem-4-carboxylic acid NMR (DMSO-$d_6$, δ): 1.02 (3H, t, J=6 Hz), 2.2–2.4 (2H, m), 2.72 (3H, s), 3.54 and 3.83 (2H, ABq, J=17 Hz), 5.24 (1H, d, J=5 Hz), 5.80 (1H, dd, J=5 and 8 Hz), 6.53 (1H, t, J=7 Hz), 7.04 (1H, s), 8.87 (1H, d, J=8 Hz), 11.57 (1H, s).

EXAMPLE 56

Benzhydryl 7β-[2-(4-fluorophenyl)acetamido]-3-[(Z)-2-(3-pyridyl)vinylthio]-3-cephem-4-carboxylate NMR (DMSO-$d_6$, δ): 3.50 and 3.56 (2H, ABq, J=12 Hz), 3.82 and 4.09 (2H, ABq, J=18 Hz), 5.20 (1H, d, J=5 Hz), 5.77 (1H, dd, J=5 and 8 Hz), 6.75 (1H, d, J=11 Hz), 6.82 (1H, d, J=11 Hz), 6.93 (1H, s), 7.1–7.5 (15H, m), 7.7–7.8 (1H, m), 8.4–8.5 (1H, m), 8.60 (1H, m), 9.21 (1H, d, J=8 Hz).

FAB-MASS (m/z): 638.1

EXAMPLE 57

To a solution of 4-carboxymethyl-2-mercaptothiazole (719 mg) in a mixture of tetrahydrofuran (14 ml) and 1,2-dimethoxyethane (14 ml) was added potassium t-butoxide (768 mg) at ice-cooling temperature with stirring and the mixture was stirred at the same temperature for 1 hour. A solution of benzhydryl 7β-[2-(2-thienyl)acetamido]-3-methanesulfonyloxy-3-cephem-4-carboxylate (2.0 g) in a mixture of tetrahydrofuran (10 ml) and 1,2-dimethoxyethane (10 ml) was added to the obtained potassium salt mixture at the same temperature and the mixture was stirred at −5–0° C. for 2 hours. The reaction mixture was poured into a mixture of ice-water (100 ml) and ethyl acetate (150 ml). The mixture was adjusted to pH 7.0 with 1N-sodium hydroxide solution. The separated organic layer was washed 0.1 N-hydrochloric acid and saturated aqueous sodium chloride, dried over magnesium sulfate and concentrated in vacuo. The residue was triturated with a mixture of diethyl ether and ethyl acetate (2:1) to give benzhydryl 7β-[2-(2-thienyl)acetamido]-3-(4-carboxymethylthiazol-2-yl)thio-3-cephem-4-carboxylate (687 mg).

NMR (DMSO-$d_6$, δ): 3.57 and 3.79 (2H, ABq, J=18 Hz), 3.7–3.8 (4H, m), 5.27 (1H, d, J=5 Hz), 5.83 (1H, dd, J=5 and 8 Hz), 6.9–7.0 (1H, m), 6.93 (1H, s), 6.97 (1H, s), 7.2–7.4 (11H, m), 7.61 (1H, s), 9.27 (1H, d, J=8 Hz).

The following compounds (Examples 58 to 62) were obtained according to a similar manner to that of Example 57.

EXAMPLE 58

Benzhydryl 7β-(2-phenylacetamido)-(3-ethoxycarbonylmethyl-1,2,4-triazol-5-yl)thio-3-cephem-4-carboxylate NMR (DMSO-$d_6$, δ): 1.18 (3H, t, J=7 Hz), 3.41 and 3.57 (2H, ABq, J17 Hz), 3.92 (2H, sb), 3.92 (2H, br s), 4.11 (2H, ABq, J=7 Hz), 5.23 (1H, d, J=5 Hz), 5.75 (1H, dd, J=5 and 8 Hz), 6.93 (1H, s), 7.2–7.6 (15H, nm), 9.17 (1H, d, J=8 Hz).

FAB-MASS (m/z): 670.1

EXAMPLE 59

Benzhydryl 7β-(2-phenylacetamido)-3-(3-carboxymethyl-1,2,4-triazol-5-yl)thio-3-cephem-4-carboxylate NMR (DMSO-$d_6$, δ): 3.3–3.6 (4H, m), 3.78 (2H, s), 5.23 (1H, d, J=5 Hz), 5.75 (1H, dd, J=5 and 8 Hz), 6.93 (1H, s), 7.2–7.5 (5H, m), 12.8 (1H, br s), 14.1 (1H, br s).

FAB-MASS (m/z): 642.0

EXAMPLE 60

Benzhydryl 7β-(2-phenylacetamido)-3-(2-carboxymethyl-1,3,4-thiadiazol-5-yl)thio-3-cephem-4-carboxylate NMR (DMSO-$d_6$, δ) 3.3–3.7 (4H, m), 4.24 (2H, s), 5.28 (1H, d, J=5 Hz), 5.87 (1H, dd, J=5 and 8 Hz), 6.95 (1H, s), 7.2–7.5 (15H, m), 9.29 (1H, d, J=5 Hz).

FAB-MASS (m/z): 658.6

EXAMPLE 61

Benzhydryl 7β-[2-(2-thienyl)acetamido]-3-[4-(2-carbamoylethyl)thiazol-2-yl]thio-3-cephem-4-carboxylate NMR (DMSO-$d_6$, δ): 2.44 (2H, t, J=7 Hz), 2.91 (2H, t, J=7 Hz), 3.52 and 3.78 (2H, ABq, J=14 Hz), 3.76 (2H, s), 5.28 (1H, d, J=5 Hz), 5.86 (1H, dd, J=5 and 8 Hz), 6.81 (1H, br s), 6.9–7.0 (3H, m), 7.2–7.5 (13H, m), 9.29 (1H, d, J=5 Hz).

FAB-MASS (m/z): 676.9

EXAMPLE 62

Benzhydryl 7β-[2-(3-thienyl)acetamido]-3-[4-(2-carbamoylethyl)thiazol-2-yl]thio-3-cephem-4-carboxylate NMR (DMSO-$d_6$, δ) 2.44 (2H, t, J=7 Hz), 2.92 (2H, t, J=7 Hz), 3.55 (2H, s), 3.51 and 3.77 (2H, ABq, J=14 Hz), 5.22 (1H, d, J=5 Hz), 5.84 (1H, dd, J=5 and 8 Hz), 6.81 (1H, br s), 6.97 (1H, s), 7.0–7.1 (1H, m), 7.2–7.5 (14H, m), 9.23 (1H, d, J=8 Hz).

FAB-MASS (m/z): 676.8

EXAMPLE 63

To a solution of 3-benzoylthiomethylpyridine (950 mg) in dimethoxymethane (8 ml) was added 28% sodium methoxide methanol solution under ice-cooling. The mixture was stirred for 30 minutes at 5–8° C. The mixture was added dropwise to a solution of benzhydryl 7β-(2-phenylacetamido)-3-methanesulfonyloxy-3-cephem-4-carboxylate in dimethoxyethane (10 ml) and N,N-dimethylformamide (8 ml) at −65° C. for 5 minutes. The mixture was stirred at −65° C. for 60 minutes. To the reaction mixture were added the cooled buffer solution (pH 4, 100 ml) and ethyl acetate (100 ml), adjusted to pH 6.7 with 1N-sodium hydroxide solution. The separated organic layer was washed with water (100 ml×3) and saturated aqueous sodium chloride, dried over magnesium sulfate and concentrated in vacuo. The residue was triturated with diethyl ether to give benzhydryl 7β-(2-phenylacetamido)-3-(3-pyridyl)methylthio-3-cephem-4-carboxylate (1.83 g).

NMR (DMSO-d$_6$, δ): 3.51 and 3.59 (2H, ABq, J=14 Hz), 3.93 and 3.83 (2H, ABq, J=18 Hz), 4.15 and 4.23 (2H, ABq, J=14 Hz), 5.16 (1H, d, J=5 Hz), 5.68 (1H, dd, J=5 and 8 Hz), 6.85 (1H, s), 7.2–7.4 (14H, m), 7.4–7.5 (2H, m), 7.6–7.7 (1H, m), 8.4–8.5 (2H, m), 9.18 (1H, d, J=8 Hz).

FAB-MASS (m/z): 608.1

The following compounds (Examples 64 to 69) were obtained according to a similar manner to that of Example 63.

EXAMPLE 64

Benzhydryl 7β-(2-phenylacetamido)-3-[2-(1-tritylpyrazol-4-yl)ethylthio]-3-cephem-4-carboxylate NMR (DMSO-d$_6$, δ): 2.5–2.7 (2H, m), 2.9–3.1 (2H, m), 3.59 and 3.51 (2H, ABq, J=14 Hz), 3.81 (2H, br s), 5.12 (1H, d, J=5 Hz), 5.66 (1H, dd, J=5 and 8 Hz), 6.85 (1H, s), 7.0–7.6 (32H, m), 9.16 (1H, d, J=8 Hz).

EXAMPLE 65

Benzhydryl 7β-(2-phenylacetamido)-3-(1,2,3-thiadiazol-5-yl)methylthio-3-cephem-4-carboxylate NMR (DMSO-d$_6$, δ): 3.50 and 3.58 (2H, ABq, J=14 Hz), 3.79 and 3.89 (2H, ABq, J=17 Hz), 4.66 (2H, s), 5.18 (1H, d, J=5 Hz), 5.71 (1H, dd, J=5 and 8 Hz), 6.87 (1H, s), 7.2–7.5 (15H, m), 8.81 (1H, s), 9.18 (1H, d, J=8 Hz).

FAB-MASS (m/z): 615.0

EXAMPLE 66

Benzhydryl 7β-(2-phenylacetamido)-3-[2-(3-pyridyl)ethylthio]-3-cephem-4-carboxylate NMR (DMSO-d$_6$, δ): 2.7–2.9 (2H, m), 3.1–3.2 (2H, m), 3.51 and 3.60 (2H, ABq, J=14 Hz), 3.87 (2H, s), 5.16 (1H, d, J=5 Hz), 5.68 (1H, dd, J=5 and 8 Hz), 6.88 (1H, s), 7.2–7.7 (17H, m), 8.4–8.5 (2H, m), 9.16 (1H, d, J=8 Hz).

FAB-MASS (m/z): 622.1

EXAMPLE 67

Benzhydryl 7β-[2-(2-thienyl)acetamido]-3-(1,2,3-thiadiazol-5-yl)methylthio-3-cephem-4-carboxylate NMR (DMSO-d$_6$, δ): 3.77 (2H, s), 3.81 and 3.91 (2H, ABq, J=14 Hz), 4.66 (2H, s), 5.20 (1H, d, J=5 Hz), 5.72 (1H, dd, J=5 and 8 Hz), 6.8–7.0 (3H, m), 7.2–7.5 (11H, m), 8.81 (1H, s), 9.20 (1H, d, J=8 Hz).

FAB-MASS (m/z) 620.9

EXAMPLE 68

Benzhydryl 7β-(2-phenylacetamido)-3-(4-carbamoylmethylthiazol-2-yl)thiomethylthio-3-cephem-4-carboxylate NMR (DMSO-d$_6$, δ): 3.4–3.9 (8H, m), 5.26 (1H, d, J=5 Hz), 5.83 (1H, dd, J=5 and 8 Hz), 6.97 (1H, s), 7.02 (1H, br s), 7.2–7.6 (16H, m), 7.56 (1H, s), 9.20 (1H, d, J=8 Hz).

EXAMPLE 69

Benzhydryl 7β-[(Z)-2-(2-cyanovinylthio)acetamido]-3-[2-(1-tritylpyrazol-4-yl)ethylthio]-3-cephem-4-carboxylate NMR (DMSO-d$_6$, δ): 2.5–2.7 (2H, m), 2.9–3.1 (2H, m), 3.75 (2H, s), 3.82 (2H, br s), 5.16 (1H, d, J=5 Hz), 5.68 (1H, dd, J=5 and 8 Hz), 5.73 (1H, d, J=10 Hz), 6.86 (1H, s), 6.9–7.6 (27H, m), 7.68 (1H, d, J=10 Hz), 9.25 (1H, d, J=8 Hz).

EXAMPLE 70

To a solution of benzhydryl 7β-[2-(2-formylaminothiazol-4-yl)acetamido]-3-(5-methyl-1,3,4-thiadiazol-2-yl)thio-3-cephem-4-carboxylate (1.2 g) in a mixture of dichloromethane (3.6 ml) and anisole (1.2 ml) was added trifluoroacetic acid (2.4 ml) under ice-cooling. The mixture was stirred at the same temperature for 45 minutes. The reaction mixture was poured into diisopropyl ether (80 ml) and the resulting precipitate was collected by filtration and dried in vacuo. The precipitate was dissolved in a mixture of aqueous sodium hydrogen carbonate (40 ml), tetrahydrofuran (20 ml) and ethyl acetate (40 ml). To the separated aqueous solution were added ethyl acetate (40 ml) and tetrahydrofuran (20 ml). The mixture was adjusted to pH 1.8 with 1N-hydrochloric acid. The organic layer was washed with saturated aqueous sodium chloride, dried over magnesium sulfate and concentrated in vacuo. The residue was triturated with ethyl acetate to give 7β-[2-(2-formylaminothiazol-4-yl)acetamido]-3-(5-methyl-1,3,4-thiadiazol-2-yl)thio-3-cephem-4-carboxylic acid (490 mg).

NMR (DMSO-d$_6$, δ): 2.72 (3H, s), 3.43 and 3.85 (2H, ABq, J=17 Hz), 3.60 (2H, s), 5.23 (1H, d, J=5 Hz), 5.80 (1H, dd, J=5 and 8 Hz), 6.95 (1H, s), 8.45 (1H, s), 9.11 (1H, d, J=8 Hz), 12.22 (1H, br s).

FAB-MASS (m/z): 499.0

The following compounds (Examples 71 to 80) were obtained according to a similar manner to that of Example 70.

EXAMPLE 71

7β-[2-(2-Acetylaminothiazol-4-yl)acetamido]-3-(5-methyl-1,3,4-thiadiazol-2-yl)thio-3-cephem-4-carboxylic acid NMR (DMSO-d$_6$, δ): 2.11 (3H, s), 2.72 (3H, s), 3.44 and 3.84 (2H, ABq, J=17 Hz), 3.58 (2H, s), 5.22 (1H, d, J=5 Hz), 5.79 (1H, dd, J=5 and 8 Hz), 6.86 (1H, s), 9.09 (1H, d, J=8 Hz), 12.09 (1H, s).

FAB-MASS (m/z): 513

EXAMPLE 72

7β-[2-(2-Thienyl)acetamido]-3-(4-carboxymethylthiazol-2-yl)thio-3-cephem-4-carboxylic acid IR (Nujol): 3300, 1780, 1695, 1640, 1530, 1240 cm$^{-1}$ NMR (DMSO-d$_6$, δ): 3.48 and 3.75 (2H, ABq, J=18 Hz), 3.7–3.8 (4H, m), 5.21 (1H, d, J=5 Hz), 5.75 (1H, dd, J=5 and 8 Hz), 6.9–7.0 (1H, m), 6.92 (1H, s), 7.3–7.4 (1H, m), 7.59 (1H, s), 9.23 (1H, d, J=8 Hz).

FAB-MASS (m/z): 498.0

EXAMPLE 73

7β-(2-Phenylacetamido)-3-(5-ethoxycarbonylmethyl-1,2,4-triazol-3-yl)thio-3-cephem-4-carboxylic acid NMR (DMSO-d$_6$, δ): 1.19 (3H, t, J=7 Hz), 3.3–3.6 (4H, m), 3.90 (2H, br s), 4.12 (2H, q, J=7 Hz), 5.16 (1H, d, J=5 Hz), 5.65 (1H, dd, J=5 and 8 Hz), 7.2–7.3 (5H, m), 9.12 (1H, d, J=8 Hz), 13.7 (1H, br s), 14.3 (1H, br s).

FAB-MASS (m/z): 504.0

EXAMPLE 74

7β-(2-Phenylacetamido)-3-[(Z)-2-(3-pyridyl)vinylthio]-3-cephem-4-carboxylic acid FAB-MASS (m/z): 454.0

EXAMPLE 75

7β-[2-(4-Fluorophenyl)acetamido]-3-[(Z)-2-(3-pyridyl)vinylthio]-3-cephem-4-carboxylic acid NMR (DMSO-$d_6$,δ): 3.50 and 3.56 (2H, ABq, J=14 Hz), 3.73 and 4.07 (2H, AB, J=18 Hz), 5.15 (1H, d, J=5 Hz), 5.70 (1H, dd, J=5 and 8 Hz), 6.78 (1H, d, J=11 Hz), 6.8 (1H, d, J=11 Hz), 7.0–7.2 (2H, m), 7.2–7.4 (2H, m), 7.4–7.5 (1H, m), 7.8–7.9 (1H, m),8.4–8.5 (1H, m), 8.65 (1H, m), 9.17 (1H, d, J=8 Hz).

FAB-MASS (m/z): 472.1

EXAMPLE 76

7β-(2-Phenylacetamido)-3-(3-pyridyl)methylthio-3-cephem-4-carboxylic acid

IR (KBr): 3284, 3057, 3032, 1784, 1757, 1666, 1606, 1537, 1379, 1348, 1242 cm$^{-1}$

NMR (DMSO-$d_6$,δ): 3.49 and 3.58 (2H, ABq, J=14 Hz), 3.79 (2H, s), 4.13 and 4.21 (2H, ABq, J=12 Hz), 5.08 (1H, d, J=5 Hz), 5.61 (1H, dd, J=5 and 8 Hz), 7.1–7.4 (5H, m), 7.3–7.5 (1H, m), 7.7–7.9 (1H, m), 8.4–8.6 (2H, m), 9.15 (1H, d, J=8 Hz).

FAB-MASS (m/z): 441.9

EXAMPLE 77

7β-[2-(2-Thienyl)acetamnido]-3-[4-(2-carbainoylethyl)thiazol-2-yl]thio-3-cephem-4-carboxylic acid IR (KBr): 3405, 3280, 1774, 1689, 1664, 1535, 1433, 1412, 1365, 1282, 1242 cm$^{-1}$ NMR (DMSO-$d_6$, δ): 2.43 (2H, t, J=7 Hz), 2.90 (2H, t, J=7 Hz), 3.47 and 3.75 (2H, ABq, J=17 Hz), 3.76 (2H, s), 5.23 (1H, d, J=5 Hz), 5.75 (1H, dd, J=5 and 8 Hz), 6.80 (1H, br s), 6.9–7.0 (2H, mn), 7.3–7.4 (3H, mn), 9.25 (1H, d, J=8 Hz).

FAB-MASS (m/z): 510.8

EXAMPLE 78

7β-[2-(3-Thienyl)acetamido]-3-[4-(2-carbainoylethyl)thiazol-2-yl]thio-3-cephemn-4-carboxylic acid IR (KBr): 3406, 3294, 1772, 1657, 1535, 1365, 1242 cm$^{-1}$ NMR (DMSO-$d_6$, δ): 2.43 (2H, t, J=7 Hz), 2.90 (2H, t, J=7 Hz), 3.47 and 3.75 (2H, ABq, J=18 Hz), 3.54 (2H, s), 5.22 (1H, d, J=5 Hz), 5.75 (1H, dd, J=5 and 8 Hz), 6.80 (1H, br s), 7.0–7.1 (1H, m), 7.2–7.3 (1H, m), 7.34 (1H, br s), 7.4–7.5 (2H, m), 9.18 (1H, d, J=8 Hz).

FAB-MASS (m/z): 510.8

EXAMPLE 79

7β-(2-Phenylacetamido)-3-(1,2,3-thiadiazol-5-yl)methylthio-3-cephem-4-carboxylic acid IR (KBr): 3440, 3890, 3340, 1770, 1680, 1535, 1360, 1240 cm$^{-1}$ NMR (DMSO-$d_6$, δ) 3.48 and 3.57 (2H, ABq, J=14 Hz), 3.76 (2H, s), 4.67 (2H, s), 5.10 (1H, d, J=5 Hz), 5.63 (1H, dd, J=5 and 8 Hz), 7.2–7.3 (5H, m), 8.85 (1H, s), 9.16 (1H, d, J=8 Hz).

FAB-MASS (m/z): 448.9

EXAMPLE 80

7β-(2-Phenylacetamido)-3-[(E)-2-(1-benzylcarbonylpyrazol-4-yl)vinylthio]-3-cephem-4-carboxylic acid IR (Nujol): 3250, 1760, 1690, 1650, 1520, 1230 cm$^{-1}$ NMR (DMSO-$d_6$, δ): 3.49 and 3.59 (2H, ABq, J=14 Hz), 3.70 and 3.96 (2H, ABq, J=17 Hz), 4.45 (2H, s), 5.15(1H, d, J=5 Hz), 5.65 (1H, dd, J=5 and 8 Hz), 6.73 (1H, d, J=15 Hz), 7.16 (1H, d, J=15 Hz), 7.2–7.4 (10 H, m), 8.20 (1H, s), 8.53 (1H, s), 9.14 (1H, d, J=8 Hz).

FAB-MASS (m/z): 561.3

EXAMPLE 81

To a solution of benzhydryl 7β-(2-phenylacetamido)-3-(3-carboxymethyl-1,2,4-triazol-5-yl)thio-3-cephem-4-carboxylate (370 mg) in a mixture of dichloromethane (1.2 ml) and anisole (0.4 ml) was added trifluoroacetic acid (0.8 ml) under ice-cooling. The mixture was stirred at room temperature for 50 minutes. The reaction mixture was poured into diisopropyl ether (30 ml), and the resulting precipitate was collected by filtration and dried in vacuo. The precipitate was dissolved in a mixture of aqueous sodium hydrogen carbonate (58 mg/30 ml), tetrahydrofuran (10 ml) and ethyl acetate (30 ml). To the separated aqueous layer was added tetrahydrofuran (10 ml) and ethyl acetate (30 ml), adjusted to pH 2.0 with 1N-hydrochloric acid. The organic layer was washed with saturated aqueous sodium chloride, dried over magnesium sulfate and concentrated in vacuo. The residue was triturated with isopropyl ether to give crude product (190 mg). The crude product (175 mg) was dissolved in a mixture of aqueous sodium bicarbonate (62 mg/10 ml), purified by high pressure liquid chromatography (HPLC) (R-ODS-C-15, YMC-pack) eluting with 20% acetonitrile-phosphate buffer (pH 3.0). The solution was concentrated in vacuo. To the resulting solution was added tetrahydrofuran (10 ml) and ethyl acetate (40 ml) and adjusted to pH 2.2 with 1N-hydrochloric acid. The organic layer was washed with saturated aqueous sodium chloride, dried over magnesium sulfate, and concentrated in vacuo. The residue was triturated with isopropyl ether to give 7β-(2-phenylacetamido)-3-(5-carboxymethyl-1,2,4-triazol-3-yl)thio-3-cephem-4-carboxylic acid (25.7 mg).

NMR (DMSO-$d_6$, δ) 3.3–3.6 (4H, m), 3.81 (2H, br s), 5.16 (1H, d, J=5 Hz), 5.65 (1H, dd, J=5 and 8 Hz), 7.1–7.3 (5H, m), 9.12 (1H, d, J=8 Hz), 14.2 (1H, br s).

FAB-MASS (m/z): 476.0

The following compounds (Examples 82 to 84) were obtained according to a similar manner to that of Example 81.

EXAMPLE 82

7β-(2-Phenylacetamido)-3-(1-carboxymethyl-1,2,3,4-tetrazol-5-yl)thio-3-cephem-4-carboxylic acid NMR (DMSO-$d_6$, δ): 3.3–3.7 (4H, m), 5.19 (1H, d, J=5 Hz), 5.40 and 5.51 (2H, AB, J=18 Hz), 5.74 (1H, dd, J=5 and 8 Hz), 7.2–7.3 (5H, m), 9.13 (1H, d, J=8 Hz).

FAB-MASS (m/z): 476.9

EXAMPLE 83

7β-(2-Phenylacetamido)-3-(5-carboxymethyl-1,3,4-thiadiazol-2-yl)thio-3-cephem-4-carboxylic acid NMR (DMSO-$d_6$, δ): 3.48 and 3.57 (2H, ABq, J=14 Hz), 3.54 and 3.87 (2H, ABq, J=18 Hz), 4.24 (2H, s), 5.23 (1H, d, J=5 Hz), 5.29 (1H, dd, J=5 and 8 Hz), 7.2–7.3 (1H, m), 9.24 (1H, d, J=8 Hz).

FAB-MASS (m/z): 492.8

EXAMPLE 84

7β-[2-(2-Thienyl)acetamido]-3-(1,2,3-thiadiazol-5-yl)methylthio-3-cephem-4-carboxylic acid IR (KBr): 3380, 1770, 1680, 1540, 1510, 1370, 1240 cm$^{-1}$ NMR (DMSO-d$_6$, δ): 3.76 (2H, br s), 3.76 (2H, br s), 4.62 (2H, s), 5.12 (1H, d, J=5 Hz), 5.64 (1H, dd, J=5 and 8 Hz), 6.9–7.0 (2H, m), 7.3–7.4 (1H, m), 8.85 (1H, s), 9.17 (1H, d, J=8 Hz).

FAB-MASS (m/z): 454.57

EXAMPLE 85

To a solution of benzhydryl 7β-(2-phenylacetamido)-3-[2-(1-tritylpyrazol-4-yl)ethylthio]-3-cephem-4-carboxylate (930 mg) in a mixture of dichloromethane (3 ml) and anisole (1 ml) was added trifluoroacetic acid (2 ml) under ice-cooling. The mixture was stirred at room temperature for 1 hour. The reaction mixture was poured into diisopropyl ether (100 ml). The precipitate was collected by filtration. The precipitate was added a 90% formic acid (4 ml) and stirred for 15 minutes at room temperature. The reaction mixture was poured into a mixture of ethyl acetate (100 ml) and ice-water (50 ml). The separated organic layer was added buffer solution (pH 6.86, 100 ml), adjusted to pH 7 with sodium bicarbonate. The separated aqueous layer was added ethyl acetate (60 ml) and tetrahydrofuran (30 ml), adjusted to pH 2.5 with 1N-hydrochloric acid. The organic layer was washed with saturated aqueous sodium chloride, dried over magnesium sulfate and concentrated in vacuo. The residue was triturated with diethyl ether to give 7β-(2-phenylacetamido)-3-[2-(pyrazol-4-yl)ethylthio]-3-cephem-4-carboxylic acid (275 mg).

IR (KBr): 3400, 3270, 1780, 1660, 1540, 1360, 1290, 1240 cm$^{-1}$

NMR (DMSO-d$_6$, δ): 2.6–2.7 (2H, m), 3.00 (2H, t, J=7 Hz), 3.49 and 3.58 (2H, ABq, J=14 Hz), 3.72 and 3.81 (2H, ABq, J=17 Hz), 5.10 (1H, d, J=5 Hz), 5.60 (1H, dd, J=5 and 8 Hz), 7.2–7.3 (5H, m), 7.47 (2H, s), 9.14 (1H, d, J=8 Hz), 13.0 (1H, br s).

The following compound was obtained according to a similar manner to that of Example 85.

EXAMPLE 86

7β-[(Z)-2-(2-Cyanovinylthio)acetamido]-3-[2-(pyrazol-4-yl)ethylthio]-3-cephem-4-carboxylic acid NMR (DMSO-d$_6$, δ): 2.6–2.7 (2H, m), 2.9–3.1 (2H, m), 3.70 and 3.82 (2H, ABq, J=18 Hz), 3.74 (2H, s), 5.14 (1H, d, J=5 Hz), 5.61 (1H, dd, J=5 and 8 Hz), 5.73 (1H, d, J=10 Hz), 7.47 (2H, s), 7.67 (1H, d, J=10 Hz), 9.23 (1H, d, J=8 Hz), 13.0 (1H, br s).

FAB-MASS (m/z): 451.9

EXAMPLE 87

To a solution of 7β-[2-(5-tert-butoxycarbonylamino-1,2,4-thiadiazol-3-yl)acetamido]-3-(5-methyl-1,3,4-thiadiazol-2-yl)thio-3-cephem-4-carboxylic acid (800 mg) in dichloromethane (2.4 ml) was added trifluoroacetic acid (10.4 ml). The mixture was stirred for 30 minutes at room temperature. The reaction mixture was poured into diisopropyl ether (150 ml). The precipitate was collected by filtration and dried. The precipitate was dissolved in a mixture of aqueous sodium hydrogen carbonate (212 mg/30 ml) and tetrahydrofuran (10 ml). The solution was washed with ethyl acetate (30 ml). To the aqueous layer was added a mixture of tetrahydrofuran (15 ml) and ethyl acetate (45 ml), adjusted to pH 2 with 1N-hydrochloric acid. The organic layer was washed with saturated aqueous sodium chloride, dried over magnesium sulfate and concentrated in vacuo. The residue was triturated with diethyl ether to give 7β-[2-(5-amino-1,2,4-thiadiazol-3-yl)acetamido]-3-(5-methyl-1,3,4-thiadiazol-2-yl)thio-3-cephem-4-carboxylic acid (490 mg).

NMR (DMSO-d$_6$, δ): 2.81 (3H, s), 3.59 and 3.67 (2H, ABq, J=17 Hz), 3.61 and 3.93 (2H, ABq, J=15 Hz), 5.32 (1H, d, J=5 Hz), 5.88 (1H, dd, J=5 and 8 Hz), 7.97 (2H, br s), 9.22 (1H, d, J=8 Hz).

FAB-MASS (m/z): 471.9

The following compound was obtained according to a similar manner to that of Example 87.

EXAMPLE 88

7β-[(Z)-2-(2-Aminothiazol-4-yl)-2-pentenoylamino]-3-(5-methyl-1,3,4-thiadiazol-2-yl)thio-3-cephem-4-carboxylic acid IR (KBr): 3410, 3110, 2970, 1780, 1620, 1520, 1400, 1320, 1260, 1200 cm$^{-1}$ NMR (DMSO-d$_6$, δ): 1.01 (3H, t, J=7 Hz), 2.34 (2H, dq, J=7 and 7 Hz), 3.53 and 3.83 (2H, ABq, J=18 Hz), 5.26 (1H, d, J=5 Hz), 5.86 (1H, dd, J=5 and 8 Hz), 6.49 (1H, s), 6.56 (1H, t, J=7 Hz), 7.13 (2H, br s), 9.13 (1H, d, J=8 Hz).

EXAMPLE 89

To a solution of 7β-amino-3-(pyrazol-4-yl)methylthio-3-cephem-4-carboxylic acid (625 mg) in dichloromethane (6 ml) was added monotrimethylsilylacetamide (2.625 g) and trimethylsilyl chloride (0.05 ml), then the solution was stirred under reflux for 1 hour to give a solution containing silylated cephem (Solution 1). To a solution of R-(−)-mandelic acid (304 mg), N,N-dimethylaminopyridine (catalytic amount), and pyridine (0.33 ml) in dichloromethane (4 ml) was added trimethylsilyl chloride (0.52 ml) and stirred at room temperature for 1 hour. N,N-Dimethylformamide (2 drops) and oxalyl chloride (0.18 ml) was added successively to the solution at 0° C., and stirred at the same temperature for 1 hour and at room temperature for 30 minutes. The solution 1 was added to the obtained solution at 0C and stirred for 2 hours at 0° C. The obtained solution was added a solution of citric acid (423 mg) in methanol (50 ml) and the mixture was stirred at 0° C. for 30 minutes.

The reaction mixture was quenched with water (100 ml), adjusted pH 7.2–7.5 with sodium hydrogen carbonate, and washed with ethyl acetate (100 ml). The aqueous layer was adjusted to pH 3.0 with 1N-hydrochloric acid and extracted with a mixture of ethyl acetate and tetrahydrofuran (10:1) (×3). The combined extracts were washed with water and brine, dried over magnesium sulfate, and evaporated under reduced pressure. The residue was crystallized from ethyl acetate and diethyl ether and purified by preparative HPLC (column, YMC P-ODS-15C and Gard Gel, mobile phase phosphate buffer (pH 6.0):acetonitrile=85:15).

The obtained eluate was adjusted to pH 3.0 with 1N-hydrochloric acid and extracted with a mixture of ethyl acetate and tetrahydrofuran (10:1) (×3). The combined extracts were washed with brine, dried over magnesium sulfate, and evaporated under reduced pressure. The residue was precipitated from chloroform, methanol, and isopropyl ether to give 7β-[(R)-2-hydroxy-2-phenylacetamido]-3-(pyrazol-4-yl)methylthio-3-cephem-4-carboxylic acid (60.5 mg) as a powder.

IR (KBr): 1770, 1680 cm$^{-1}$

NMR (DMSO-d$_6$, δ): 3.76 (3H, s), 4.01 (2H, s), 5.06–5.11 (2H, m), 5.59 (1H, dd, J=4.7 and 8.8 Hz), 6.15 (1H, d, J=5.5 Hz), 7.20–7.47 (5H, m), 7.55 (2H, s), 8.77 (1H, d, J=8.9 Hz).

FAB-MASS (m/z): 447 (M+H)$^+$

The following compound was obtained according to a similar manner to that of Example 89.

EXAMPLE 90

7β-[(S)-2-Hydroxy-2-phenylacetamido]-3-(pyrazol-4-yl) methylthio-3-cephem-4-carboxylic acid IR (KBr): 1770, 1678 cm$^{-1}$ NMR (DMSO-d$_6$, δ): 3.80 (2H, s), 4.02 (2H, s), 5.04–5.10 (2H, m), 5.54 (1H, dd, J=4.6 and 8.7 Hz), 7.20–7.46 (5H, m), 7.56 (2H, s), 8.67 (1H, d, J=8.7 Hz).

FAB-MASS (m/z): 447 (M+H)$^+$

EXAMPLE 91

To a solution of benzhydryl 7β-(2-phenylacetamido)-3-(4-carboxymethylthiazol-2-yl)thio-3-cephem-4-carboxylate (1.0 g) in dichloromethane (20 ml) and N,N-dimethylformamide (20 ml) were added 1-hydroxybenzotriazole (247 mg), WSC.HCl (349 mg) and 2M-methylamine tetrahydrofuran solution (0.91 ml) at room temperature. After stirring at room temperature for 2 hours, the solution was poured into a mixture of water and ethyl acetate. The separated organic layer was washed with saturated sodium chloride solution (×3), dried over magnesium sulfate and evaporated under reduced pressure. Ethyl acetate was added to the residue and the resulting crystal was collected by filtration to give benzhydryl 7β-(2-phenylacetamido)-3-[4-(N-methylcarbamoylmethyl)thiazol-2-yl]thio-3-cephem-4-carboxylate (186 mg).

NMR (DMSO-d$_6$, δ): 2.59 (3H, d, J=4.6 Hz), 3.53 (2H, d, J=3.7 Hz), 3.58 (2H, s), 3.48 and 3.77 (2H, ABq, J=17.7 Hz), 5.25 (1H, d, J=5.0 Hz), 5.81 (1H, dd, J=5.0 and 8.5 Hz), 6.97 (1H, s), 7.2–7.5 (15H, m), 7.55 (1H, s), 7.92 (1H, m), 9.24 (1H, d, J=8.5 Hz).

EXAMPLE 92

To a solution of benzhydryl 7β-(2-phenylacetamido)-3-(4-carboxymethylthiazol-2-yl)thio-3-cephem-4-carboxylate (500 mg) in N,N-dimethylformamide (10 ml) were added 1-hydroxybenzotriazole (123 mg), WSC.HCl (175 mg) and morpholine (79 mg) at room temperature. After stirring at room temperature for 2.5 hours, the solution was poured into a mixture of water and ethyl acetate, and adjusted to pH 7.0 with aqueous sodium hydrogen carbonate. The separated organic layer was washed with saturated sodium chloride solution (×3), dried over magnesium sulfate and evaporated under reduced pressure. The residue was subjected to column chromatography on silica gel (eluent: ethyl acetate/n-hexane) to give benzhydryl 7β-(2-phenylacetamido)-3-(4-morpholinocarbonylmethylthiazol-2-yl)thio-3-cephem-4-carboxylate (147 mg).

NMR (DMSO-d$_6$, δ): 3.4–3.6 (10H, m), 3.48 and 3.76 (2H, ABq, J=17.3 Hz), 3.87 (2H, s), 5.25 (1H, d, J=5.0 Hz), 5.81 (1H, dd, J=5.0 and 8.5 Hz), 6.97 (1H, s), 7.2–7.5 (15H, m), 7.57 (1H, s), 9.23 (1H, d, J=8.5 Hz).

EXAMPLE 93

To a solution of benzhydryl 7β-(2-phenylacetamido)-3-(4-carboxymethylthiazol-2-yl)thio-3-cephem-4-carboxylate (500 mg) in dichloromethane (10 ml) and N,N-dimethylformamide (10 ml) were added 1-hydroxybenzotriazole (123 mg), WSC.HCl (175 mg) and 2-aminomethylpyridine (99 mg) at room temperature. After stirring at room temperature for 3 hours, the solution was poured into a mixture of water and ethyl acetate, and adjusted to pH 7.0 with aqueous sodium hydrogen carbonate. The separated organic layer was washed with saturated sodium chloride solution (×3), dried over magnesium sulfate and evaporated under reduced pressure. Ethyl acetate was added to the residue and the resulting crystal was collected by filtration to give benzhydryl 7β-(2-phenylacetamido)-3-[4-[N-(2-pyridylmethyl)carbamoylmethyl]thiazol-2-yl]thio-3-cephem-4-carboxylate (178 mg).

NMR (DMSO-d$_6$, δ): 3.53 (2H, d, J=3.8 Hz), 3.54 and 3.78 (2H, ABq, J=17.5 Hz), 3.72 (2H, s), 4.39 (2H, d, J=5.9 Hz), 5.23 (1H, d, J=5.0 Hz), 5.81 (1H, dd, J=5.0 and 8.4 Hz), 6.94 (1H, s), 7.2–7.5 (17H, m), 7.61 (1H, s), 7.71 (1H, dt, J=1.8 and 7.7 Hz), 8.48 (1H, d, J=4.0 Hz), 8.67 (1H, t, J=6.0 Hz), 9.26 (1H, d, J=8.4 Hz).

EXAMPLE 94

To a mixture of benzhydryl 7β-(2-phenylacetamido)-3-(5-aminothiazol-2-yl)thio-3-cephem-4-carboxylate (1.47 g) and dichloromethane (4.41 ml) were added trifluoroacetic acid (2.94 ml) and anisole (1.47 ml) under ice-cooling. After stirring at room temperature for 1 hour, the solution was poured into diisopropyl ether. The resulting precipitate was collected by filtration, added to a mixture of tetrahydrofuran, ethyl acetate and water, and adjusted to pH 7.2 with an aqueous sodium hydrogen carbonate. The separated aqueous layer was washed with ethyl acetate, adjusted to pH 3.0 with 1N-hydrochloric acid and extracted with tetrahydrofuran. The tetrahydrofuran solution was washed with saturated sodium chloride solution, dried over magnesium sulfate and evaporated under reduced pressure. The residue was subjected to column chromatography on HP-20 (eluent: 20% isopropanol-water).

The object fraction was evaporated under reduced pressure. To the aqueous layer was added ethyl acetate and the mixture was adjusted to pH 2.8 with 1N-hydrochloric acid. The extracted ethyl acetate solution was washed with saturated sodium chloride solution, dried over magnesium sulfate and evaporated under reduced pressure. Ethyl acetate was added to the residue and the resulting crystal was collected by filtration to give 7β-(2-phenylacetamido)-3-(5-aminothiazol-2-yl)thio-3-cephem-4-carboxylic acid (194 mg).

IR (KBr): 1774, 1678, 1656, 1515 cm$^{-1}$

NMR (DMSO-d$_6$, δ): 3.41 (2H, s), 3.51 (2H, d, J=3.8 Hz), 5.13 (1H, d, J=4.7 Hz), 5.62 (1H, dd, J=4.7 and 8.3 Hz), 6.84 (1H, s), 7.1–7.4 (7H, m), 9.09 (1H, d, J=8.3 Hz).

FAB-MASS (m/z): 449 (M+H)$^+$

EXAMPLE 95

To a solution of 4-carboxymethyl-2-mercapto-4,5,6,7-tetrahydrobenzothiazole (780 mg) in tetrahydrofuran (11.7 ml) and dimethoxyethane (11.7 ml) was added potassium t-butoxide (667 mg) at −10° C., and the solution was stirred at the same temperature for 20 minutes. On the other hand, a solution of benzhydryl 7β-(2-phenylacetamido)-3-methanesulfonyloxy-3-cephem-4-carboxylate (1.64 g) in tetrahydrofuran (8.2 ml) and dimethoxyethane (8.2 ml) was added to the above solution at −15° C. After stirring under ice-cooling for 2 hours, the solution was poured into a mixture of water and ethyl acetate. The separated organic layer was washed with saturated sodium chloride solution, dried over magnesium sulfate and evaporated under reduced pressure to give potassium benzhydryl 7β-(2-phenylacetamido)-3-(4-carboxymethyl-4,5,6,7-tetrahydrobenzothiazol-2-yl)thio-3-cephem-4-carboxylate (2.02 g).

NMR (DMSO-$d_6$, δ): 1.4–2.1 (4H, m), 2.1–2.5 (1H, m), 2.6–2.8 (2H, m), 2.8–3.0 (1H, m), 3.0–3.3 (1H, m), 3.4–3.8 (4H, m), 5.1–5.4 (1H, m), 5.7–5.9 (1H, m), 6.8–7.0 (1H, m), 7.1–7.5 (15H, m), 9.2–9.3 (1H, m).

FAB-MASS (m/z): 750 (M+H)$^+$

EXAMPLE 96

To a solution of 4-(2-carboxyethyl)-2-mercaptothiazol (972 mg) in tetrahydrofuran (14.6 ml) and dimethoxyethane (14.6 ml) was added potassium t-butoxide (960 mg) at −10° C., and the mixture was stirred at the same temperature for 20 minutes. On the other hand, a solution benzhydryl 7β-[2-(3-thienyl)acetamido]-3-methanesulfonyloxy-3-cephem-4-carboxylate (2.5 g) in tetrahydrofuran (35 ml) was added to the above mixture at −15° C. After stirring under ice-cooling for 2 hours, the solution was poured into a mixture of water and ethyl acetate. The separated organic layer was washed with saturated sodium chloride solution, dried over magnesium sulfate and evaporated under reduced pressure. Diisopropyl ether was added to the residue and the resulting precipitate was collected by filtration to give potassium benzhydryl 7β-[2-(3-thienyl)acetamido]-3-[4-(2-carboxyethyl)thiazol-2-yl]thio-3-cephem-4-carboxylate (2.69 g).

NMR (DMSO-$d_6$, δ): 2.61 (2H, t, J=7.7 Hz), 2.89 (2H, t, J=7.8 Hz), 3.57 (2H, s), 3.50 and 3.77 (2H, ABq, J=17.7 Hz), 5.27 (1H, d, J=4.9 Hz), 5.82 (1H, dd, J=4.9 and 7.7 Hz), 6.97 (1H, s), 7.1–7.6 (14H, m), 9.21 (1H, d, J=7.7 Hz).

FAB-MASS (m/z): 716 (M+H)$^+$

EXAMPLE 97

To a solution of benzhydryl 7β-amino-3-[(Z)-2-(3-pyridyl)vinylthio]-3-cephem-4-carboxylate (500 mg) in tetrahydrofuran (12.5 ml) was added N-trimethylsilylacetamide (550 mg), and stirred at room temperature for 20 minutes. To the solution was added dropwise a solution of phenyl acetyl chloride (146 μl) above at −20° C. for 2 minutes. The mixture was stirred at −20~−15° C. for 50 minutes. To the reaction mixture were added water (50 ml), ethyl acetate (50 ml) and tetrahydrofuran (15 ml). The organic layer was separated, washed with water and saturated aqueous solution of sodium chloride, dried over magnesium sulfate and concentrated in vacuo. The residue was triturated with ethyl acetate to give benzhydryl 7β-(2-phenylacetamido)-3-[(Z)-2-(3-pyridyl)vinylthio]-3-cephem-4-carboxylate (532 mg).

NMR (DMSO-$d_6$, δ): 3.50 and 3.59 (2H, ABq, J=14 Hz), 3.82 and 4.10 (2H, ABq, J=18 Hz), 5.21 (1H, d, J=5 Hz), 5.78 (1H, dd, J=5 and 8 Hz), 6.76 (1H, d, J=11 Hz), 6.81 (1H, d, J=11 Hz), 6.94 (1H, s), 7.2–7.5 (16H, m), 7.7–7.8 (1H, m), 8.4–8.5 (1H, m), 8.59 (1H, m), 9.22 (1H, d, J=8 Hz).

APCI-MASS (m/z): 620 (M$^+$)

EXAMPLE 98

To a solution of benzhydryl 7β-amino-3-[(E)-2-(4-pyrazolyl)vinylthio]-3-cephem-4-carboxylate (515 mg) in tetrahydrofuran (12.5 ml) was added N-trimethylsilylacetamide (550 mg), and stirred at room temperature for 15 minutes. To the solution was added dropwise a solution of phenylacetyl chloride (146 μl) above at −20° C. for 2 minutes. The mixture was stirred at −20~−15° C. for 1 hour. To the reaction mixture were added water (100 ml) and ethyl acetate (100 ml). The organic layer was separated, washed with buffer solution (pH 7) and saturated aqueous solution of sodium chloride, dried over magnesium sulfate and concentrated in vacuo. The residue was subjected to column chromatography on silica gel (eluent: dichloromethane:ethyl acetate=9:1) to give benzhydryl 7β-(2-phenylacetamido)-3-[(E)-2-(1-benzylcarbonylpyrazol-4-yl)vinylthio]-3-cephem-4-carboxylate (93.4 mg).

NMR (DMSO-$d_6$, δ): 3.51 and 3.60 (2H, ABq, J=14 Hz), 3.80 and 3.99 (2H, ABq, J=18 Hz), 4.45 (2H, s), 5.21 (1H, d, J=5 Hz), 5.72 (1H, dd, J=5 and 8 Hz), 6.74 (1H, d, J=15 Hz), 6.90 (1H, s), 7.18 (1H, d, J=15 Hz), 7.2–7.6 (15H, m), 8.20 (1H, s), 8.55 (1H, s), 9.19 (1H, d, J=8 Hz).

APCI-MASS (m/z): 609 (M$^+$)

EXAMPLE 99

To a solution of benzhydryl 7β-(2-phenylacetamido)-3-trifluoromethanesulfonyloxy-3-cephem-4-carboxylate (2.0 g) in a mixture of tetrahydrofuran (20 ml), dimethoxyethane (20 ml) and N,N-dimethylformamide (20 ml) was added 1-carboxymethyl-5-mercapto-1,2,3,4-tetrazole dipotassium salt (608 mg) with stirring at −25° C. The mixture was stirred at −25~−15° C. for 30 minutes and −15~−8° C. for 2 hours. To a mixture of ethyl acetate (100 ml) and ice-water (100 ml) was added the reaction mixture with stirring. To the separated aqueous solution was added ethyl acetate (150 ml). The mixture was adjusted to pH 1.8 with 1N-hydrochloric acid. The organic layer was separated, washed successively with water, saturated aqueous sodium chloride, dried over anhydrous magnesium sulfate and concentrated in vacuo. The residue was triturated with isopropyl ether to give benzhydryl 7β-(2-phenylacetamido)-3-(1-carboxymethyl-1,2,3,4-tetrazol-5-yl)thio-3-cephem-4-carboxylate (412 mg).

NMR (DMSO-$d_6$, δ): 3.3–3.7 (4H, m), 5.2–5.5 (2H, m), 5.24 (1H, d, J=5 Hz), 5.83 (1H, dd, J=5 and 8 Hz), 6.95 (1H, s), 7.2–7.5 (15H, m), 9.19 (1H, d, J=8 Hz).

FAB-MASS (m/z): 643.1

EXAMPLE 100

To a solution of benzhydryl 7β-(2-phenylacetamido)-3-[2-(3-pyridyl)ethylthio]-3-cephem-4-carboxylate (632 mg) in a mixture of dichloromethane (1.8 ml) and anisole (0.6 ml) was added trifluoroacetic acid (1.2 ml) under ice-cooling. The mixture was stirred at the same temperature for 1.5 hours. The reaction mixture was poured into diisopropyl ether (60 ml), and the resulting precipitate was collected by filtration and dried in vacuo. The precipitate was dissolved in a mixture of aqueous sodium hydrogen carbonate (188 mg/50 ml), tetrahydrofuran (20 ml) and ethyl acetate (40 ml). To the separated aqueous layer was added tetrahydrofuran (20 ml) and ethyl acetate (40 ml), adjusted to pH 3.0 with 1N-hydrochloric acid. The resulting precipitate was collected by filtration, washed with water, ethyl acetate and n-hexane, and dried to give 7β-(2-phenylacetamido)-3-[2-(3-pyridyl)ethylthio]-3-cephem-4-carboxylic acid (366 mg).

NMR (DMSO-$d_6$, δ) 2.7–2.9 (2H, m), 3.0–3.2 (2H, m), 3.49 and 3.58 (2H, ABq, J=14 Hz), 3.75 and 3.85 (2H, ABq, J=17 Hz), 5.11 (1H, d, J=5 Hz), 5.62 (1H, d, J=5 and 8 Hz), 7.2–7.4 (6H, m), 7.6–7.8 (1H, m), 8.4–8.5 (2H, m), 9.13 (1H, d, J=8 Hz).

FAB-MASS (m/z): 456.0

EXAMPLE 101

To a solution of benzhydryl 7β-(2-phenylacetamido)-3-[4-(carbamoylmethylthiazol-2-yl)thiomethylthio]-3-cephem-4-carboxylate (125 mg) in a mixture of dichloromethane (0.4 ml) and anisole (0.125 ml) was added trifluoroacetic acid (0.25 ml) under ice-cooling. The mixture was stirred at the same temperature for 1 hour. The reaction mixture was poured into diisopropyl ether (50 ml) and the resulting precipitate was collect by filtration to give 7β-(2-phenylacetamido)-3-[4-(carbamoylmethylthiazol-2-yl)thiomethylthio]-3-cephem-4-carboxylic acid (89.0 mg).

NMR (DMSO-$d_6$, δ): 3.4–3.6 (6H, m), 3.40 and 3.76 (2H, ABq, J=18 Hz), 5.20 (1H, d, J=5 Hz), 5.74 (1H, dd, J=5 and 8 Hz), 6.99 (1H, br s), 7.1–7.3 (5H, m), 7.44 (1H, br s), 7.53 (1H, s), 9.22 (1H, d, J=8 Hz).

EXAMPLE 102

To a suspension of 7β-(2-phenylacetamido)-3-[4-(carbamoylmethylthiazol-2-yl)thio]-3-cephem-4-carboxylic acid (1.84 g), water (18 ml) and acetone (10 ml) was added sodium acetate (924 mg), and dissolved. The solution was stirred for 1 hour at ambient temperature. The resulting precipitate was collected by filtration, washed with acetone, and dried over in vacuo to give sodium 7β-(2-phenylacetamido)-3-[4-(carbamoylmethylthiazol-2-yl)thio]-3-cephem-4-carboxylate (890 mg).

IR (Nujol): 3250, 1750, 1650, 1605, 1530, 1350, 1260 cm$^{-1}$

NMR ($D_2O$, δ): 3.40 and 3.76 (2H, ABq, J=17 Hz), 3.6–3.8 (4H, m), 5.19 (1H, d, J=5 Hz), 5.68 (1H, d, J=5 Hz), 7.3–7.5 (6H, m).

FAB-MASS (m/z): 512.6

EXAMPLE 103

To a solution of 7β-(2-phenylacetamido)-3-[4-(carboxymethylthiazol-2-yl)thio]-3-cephem-4-carboxylic acid (950 mg) in tetrahydrofuran (37 ml) and methanol (20 ml) was added solution of sodium acetate (317 mg) in methanol (20 ml). The mixture was stirred at ambient temperature for 20 minutes. The resulting precipitate collected by filtration, washed successively with methanol and n-hexane, dried in vacuo to give sodium 7β-(2-phenylacetamido)-3-[4-(carboxymethylthiazol-2-yl)thio]-3-cephem-4-carboxylate (0.77 g).

IR (KBr): 3400, 3330, 1770, 1710, 1650, 1600, 1580, 1530, 1390, 1350, 1260, 1220 cm$^{-1}$

NMR ($D_2O$, δ): 3.42 and 3.75 (2H, ABq, J=18 Hz), 3.6–3.8 (4H, m), 5.19 (1H, d, J=5 Hz), 5.67 (1H, d, J=5 Hz), 7.3–7.5 (6H, m).

FAB-MASS (m/z): 535.9

EXAMPLE 104

To a solution of 2-mercapto-5-methyl-1,3,4-thiadiazol (142 mg) in dimethoxyethane (3 ml) was added potassium t-butoxide (120 mg) at −20° C. stirring and the mixture was stirred at −20~−10° C. for 30 minutes to give the potassium salt solution. On the other hand, to a suspension of 7β-(2-phenylacetamido)-3-trifluoromethanesulfonyloxy-3-cephem-4-carboxylic acid (500 mg) in dimethoxyethane (4 ml) and dichloromethane (7.5 ml) was added N-trimethylsilylacetamide (562 mg). The suspension was stirred at room temperature for 30 minutes. To the mixture was added the potassium salt solution prepared above at −20° C. and the mixture was −20~−10° C. for 30 minutes and 0~5° C. for 1.5 hours. The mixture was poured into a mixture of ice-water (20 ml) and ethyl acetate (30 ml). The organic layer was separated, added water (20 ml). To the mixture was adjusted to pH 6.8 with 1N-sodium hydroxide solution. The aqueous layer was separated, evaporated in vacuo to remove the organic solvent. The resulting residue was purified by high pressure liquid chromatography (HPLC) (R-ODS-C-15, YMC-pack) eluting with 27% acetonitrile-phosphate buffer (pH 3.0). The solution was extracted with ethyl acetate (100 ml). The extract was concentrated in vacuo. The residue was solved with acetonitrile (60 ml) and water (20 ml). The solution was concentrated in vacuo. The residue was triturated with water to give 7β-(2-phenylacetamido)-3-(5-methyl-1,3,4-thiadiazol-2-yl)thio-3-cephem-4-carboxylic acid (262 mg).

NMR (DMSO-$d_6$, δ): 2.72 (3H, s), 3.48 and 3.57 (2H, ABq, J=14 Hz), 3.53 and 3.85 (2H, ABq, J=18 Hz), 5.21 (1H, d, J=5 Hz), 5.78 (1H, dd, J=5 and 8 Hz), 7.2–7.4 (5H, m), 9.23 (1H, d, J=8 Hz).

EXAMPLE 105

To a solution of 7β-(2-phenylacetamido)-3-(5-methyl-1,3,4-thiadiazol-2-yl)thio-3-cephem-4-carboxylic acid (492 mg) in N,N-dimethylacetamide (4 ml) was added cesium carbonate (200 mg) under ice-cooling, stirred at the same temperature for 1.5 hours. To the mixture was added iodomethyl pivalate (297 mg), stirred for 1 hour at the same temperature. To the mixture were added water (50 ml) and ethyl acetate (50 ml). The organic layer was separated, washed with water and saturated aqueous solution of sodium chloride, dried over magnesium sulfate and concentrated in vacuo. The residue was triturated with diethyl ether to give pivaloyloxymethyl 7β-(2-phenylacetamido)-3-(5-methyl-1,3,4-thiadiazol-2-yl)thio-3-cephem-4-carboxylate (492 mg).

NMR ($CDCl_3$, δ): 1.21 (9H, s), 2.78 (3H, s), 3.46 and 3.75 (2H, ABq, J=18 Hz), 3.60 and 3.69 (2H, ABq, J=16 Hz), 5.01 (1H, d, J=5 Hz), 5.8–6.0 (3H, m), 6.12 (1H, d, J=9 Hz), 7.2–7.4 (5H, m).

FAB-MASS (m/z): 563.0

EXAMPLE 106

To a solution of benzhydryl 7β-[2-(2-aminothiazol-4-yl)acetamido]-3-(5-methyl-1,3,4-thiadiazol-2-yl)thio-3-cephem-4-carboxylic acid (1.0 g) in a mixture of tetrahydrofuran (15 ml) and N,N-dimethylformamide (5 ml) was added acetyl chloride (245 μl) and pyridine (254 μl) under ice-cooling. The mixture was stirred at the same temperature for 4 hours. The reaction mixture was added to a mixture of ethyl acetate (70 ml) and ice-water (50 ml). The organic layer was separated, washed with water and saturated aqueous solution of sodium chloride, dried over magnesium sulfate and concentrated in vacuo. The residue was triturated with ethyl acetate to give benzhydryl 7β-[2-(2-acetylaminothiazol-4-yl)acetamido]-3-(5-methyl-1,3,4-thiadiazol-2-yl)thio-3-cephem-4-carboxylate (675 mg).

NMR (DMSO-$d_6$, δ): 2.11 (3H, s), 2.71 (3H, s), 3.58 and 3.87 (2H, ABq, J=17 Hz), 3.59 (2H, s), 5.28 (1H, d, J=5 Hz), 5.87 (1H, dd, J=5 and 8 Hz), 6.87 (1H, s), 6.97 (1H, s), 7.2–7.4 (10H, m), 9.14 (1H, d, J=8 Hz), 12.09 (1H, s).

FAB-MASS (m/z): 679.1

EXAMPLE 107

To a suspension of 7β-[2-(5-chloro-2-formylaminothiazol-4-yl)acetamido]-3-(5-methyl-1,3,4- thiadiazol-2-yl)thio-3-cephem-4-carboxylic acid (380 mg), methanol (4 ml) and tetrahydrofuran (4 ml) was conc-hydrochloric acid (153 μl). The mixture was stirred for 5 hours at 35° C. The reaction mixture was added to a mixture of ethyl acetate (20 ml) and ice-water (50 ml). To the aqueous solution was added ethyl acetate (20 ml). The mixture was adjusted to pH 7 with 1N-sodium hydroxide solution. To the separated aqueous solution was added ethyl acetate (20 ml). The mixture was adjusted to pH 2 with 1N-hydrochloric acid. The precipitate was collected by filtration, washed with ethyl acetate, and dried to give 7β-[2-(2-amino-5-chlorothiazol-4-yl)acetamido]-3-(5-methyl-1,3,4-thiadiazol-2-yl)thio-3-cephem-4-carboxylic acid (188 mg).

NMR (DMSO-$d_6$, δ): 2.72 (3H, s), 3.38 (2H, s), 3.53 and 3.85 (2H, ABq, J=18 Hz), 5.23 (1H, d, J=5 Hz), 5.78 (1H, dd, J=5 and 8 Hz), 7.16 (2H, br s), 9.06 (1H, d, J=8 Hz).

EXAMPLE 108

To a solution of 4-(2-mercaptothiazol-4-yl)benzoic acid (980 mg) in tetrahydrofuran (13.7 ml) and dimethoxyethane (13.7 ml) was added potassium t-butoxide (642 mg) at −10° C., and the solution was stirred at the same temperature for 20 minutes. On the other hand, a solution of benzhydryl 7β-(2-phenylacetamido)-3-methanesulfonyloxy-3-cephem-4-carboxylate (1.8 g) in tetrahydrofuran (20 ml) was added to the above solution at −15° C. After stirring under ice-cooling for 2.5 hours, the solution was poured into a mixture of water (70 ml) and ethyl acetate (70 ml), and adjusted to pH 7.0 with 1N-hydrochloric acid. The separated organic layer was washed with saturated sodium chloride solution, dried over magnesium sulfate and evaporated under reduced pressure. The residue was subjected to a column chromatography on silica gel and eluted with a mixture of ethyl acetate and methanol (4.5:1). The fractions containing the object compound were combined and evaporated in vacuo to give potassium benzhydryl 7β-(2-phenylacetamido)-3-[4-(4-carboxyphenyl)thiazol-2-yl]thio-3-cephem-4-carboxylate (465 mg).

IR (KBr): 1787, 1739, 1685, 1409, 1375, 1224 cm$^{-1}$

NMR (DMSO-$d_6$, δ): 3.56 (2H, br s), 3.68 and 3.92 (2H, ABq, J=17.7 Hz), 5.30 (1H, d, J=5.0 Hz), 5.86 (1H, dd, J=5.0 and 8.3 Hz), 6.98 (1H, s), 7.15–7.50 (15H, m), 7.85–8.15 (4H, m), 8.30 (1H, s), 9.28 (1H, d, J=8.3 Hz).

EXAMPLE 109

To a mixture of potassium benzhydryl 7β-(2-phenylacetamido)-3-[4-(4-carboxyphenyl)thiazol-2-yl]thio-3-cephem-4-carboxylate (450 mg), anisole (0.45 ml) and dichloromethane (1.35 ml) was added trifluoroacetic acid (0.9 ml) at 15° C. After stirring at room temperature for 1.5 hours, the solution was poured into diisopropyl ether. The resulting precipitate was collected by filtration, added to a mixture of tetrahydrofuran (10 ml) and water (15 ml), and the solution was adjusted to pH 7.2 with an aqueous sodium hydrogen carbonate. The separated aqueous solution was adjusted to pH 3.0 with 1N-hydrochloric acid and extracted with tetrahydrofuran. The tetrahydrofuran solution was washed with saturated sodium chloride solution, dried over magnesium sulfate and evaporated under reduced pressure. Ethyl acetate was added to the residue and the resulting powder was collected by filtration and dried in vacuo to give 7β-(2-phenylacetamido)-3-[4-(4-carboxyphenyl)thiazol-2-yl]thio-3-cephem-4-carboxylic acid (75 mg).

IR (KBr): 1776, 1685, 1660, 1610, 1351, 1247 cm$^{-1}$

NMR (DMSO-$d_6$, δ): 3.53 (2H, dd, J=13.9 and 18.6 Hz), 3.62 and 3.90 (2H, ABq, J=17.7 Hz), 5.26 (1H, d, J=5.0 Hz), 5.77 (1H, dd, J=5.0 and 8.3 Hz), 7.15–7.35 (5H, m), 8.04 (4H, dd, J=8.7 and 13.3 Hz), 8.40 (1H, s), 9.23 (1H, d, J=8.3 Hz).

FAB-MASS (m/z): 554 (M+H)$^+$

The following compound was obtained according to a similar manner to that of Example 103.

EXAMPLE 110

Sodium 7β-[2-(2-thienyl)acetamido]-3-[4-(2-carboxyethyl)thiazol-2-yl]thio-3-cephem-4-carboxylate IR (KBr): 1778, 1658, 1527, 1388, 1249 cm$^{-1}$ NMR (DMSO-$d_6$, δ): 2.50–2.65 (2H, m), 2.80–2.95 (2H, m), 3.26 and 3.70 (2H, ABq, J=16.8 Hz), 3.76 (2H, s), 5.08 (1H, d, J=4.97 Hz), 5.56 (1H, dd, J=5.0 and 8.4 Hz), 6.85–7.00 (2H, m), 7.24 (1H, s), 7.30–7.40 (1H, m), 9.17 (1H, d, J=8.4 Hz).

EXAMPLE 111

To a solution of 7β-[2-(2-thienyl)acetamido]-3-[4-(2-carboxyethyl)thiazol-2-yl]thio-3-cephem-4-carboxylic acid (100 mg) in water (50 ml) was added 0.1 mol/l-sodium hydroxide solution (3.9 ml). The solution was lyophilized to give disodium 7β-[2-(2-thienyl)acetamido]-3-[4-(2-carboxyethyl)thiazol-2-yl]thio-3-cephem-4-carboxylate (108.3 mg).

IR (KBr): 1766, 1662, 1612, 1552, 1348, 1238 cm$^{-1}$

NMR (DMSO-$d_6$, δ): 2.10–2.30 (2H, m), 2.70–2.90 (2H, m), 3.27 and 3.70 (2H, ABq, J=16.8 Hz), 3.76 (2H, s), 5.08 (1H, d, J=5.0 Hz), 5.56 (1H, dd, J=5.0 and 8.4 Hz), 6.90–7.0 (2H, m), 7.15 (1H, s), 7.30–7.40 (1H, m), 9.20 (1H, d, J=8.4 Hz).

FAB-MASS (m/z): 534 (M+H)$^+$

EXAMPLE 112

To a solution of 7β-(2-phenylacetamido)-3-(4-carboxymethylthiazol-2-yl)thio-3-cephem-4-carboxylic acid (100 mg) in water (50 ml) was added 0.1 mol/l-sodium hydroxide solution (4.06 ml). The solution was lyophilized. The above obtained powder was dissolved in a mixture of methanol (0.5 ml) and acetone (1.3 ml) under stirring at 30° C. The stirring was continued for 2 hours at room temperature to give crystals, which were collected by filtration and dried to give disodium 7β-(2-phenylacetamido)-3-(4-carboxymethylthiazol-2-yl)thio-3-cephem-4-carboxylate (69.1 mg).

IR (KBr) 1753, 1656, 1623, 1535, 1390, 1261 cm$^1$

NMR (DMSO-$d_6$, δ): 3.25 and 3.71 (2H, ABq, J=17.0 Hz), 3.53 (2H, dd, J=14 and 17.0 Hz), 3.65 (2H, s), 5.05 (1H, d, J=5.0 Hz), 5.54 (1H, dd, J=5.0 and 8.4 Hz), 7.05–7.35 (5H, m), 7.37 (1H, s), 9.15 (1H, d, J=8.4 Hz).

FAB-MASS (m/z): 536 (M+H)$^+$

What is claimed is:

1. A cephem compound of the following formula (I), or a salt thereof:

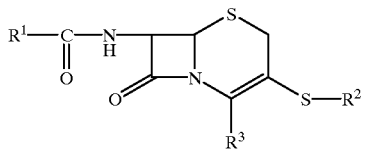

(I)

wherein

R¹ is a phenyl(lower)alkyl,

R² is a thiazolyl substituted by carboxy(lower)alkyl, thiazolyl substituted by carbamoyl(lower)alkyl, or thiazolyl substituted by N,N-di(lower)alkylcarbamoyl(lower)alkyl, and R³ is carboxy.

2. A method for the prophylactic and/or therapeutic treatment of the diseases caused by *Helicobacter pylori* infection which comprises administering a cephem compound of claim 1 or a pharmaceutically acceptable salt thereof to a human being or an animal.

3. A method for treatment or inhibition of the diseases caused by *Helicobacter pylori* infection which comprises administering an effective amount of the cephem compound (I) of claim 1 to a patient in need of said treatment or inhibition.

4. A process for preparing a compound of claim 1, or a salt thereof, which comprises (i) reacting a compound of the formula (II):

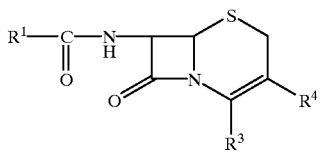

(II)

wherein

R¹ and R³ are each as defined in claim 1, and

R⁴ is a leaving group, or a salt thereof, with a compound of the formula (III):

(III)

wherein R² is defined in claim 1, or a salt thereof, or (ii) subjecting a compound of the formula (Ia):

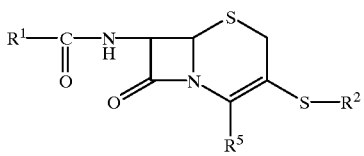

(Ia)

wherein

R¹ and R² are each as defined in claim 1, and

R⁵ is protected carboxy, or a salt thereof, to elimination reaction of the carboxy-protective group, to give a compound of the formula (Ib):

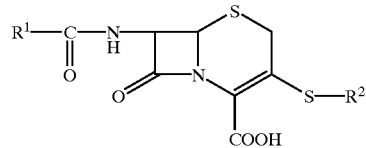

(Ib)

wherein

R¹ and R² are each as defined in claim 1, or a salt thereof, or (iii) reacting a compound of the formula (IV):

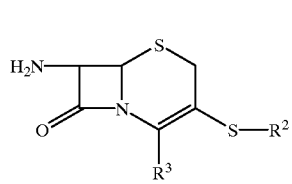

(IV)

wherein R² and R³ are each as defined in claim 1, or its reactive derivative at the amino-group or a salt thereof, with a compound of the formula (V):

R¹—COOH    (V)

wherein R¹ is defined in claim 1, or its reactive derivative at the carboxy-group or a salt thereof, or (iv) subjecting a compound of the formula (Ib):

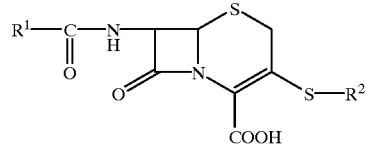

(Ib)

wherein R¹ and R² are each as defined in claim 1, or its reactive derivative at the carboxy group or a salt thereof, to protecting reaction of the carboxy, to give a compound of the formula (Ia):

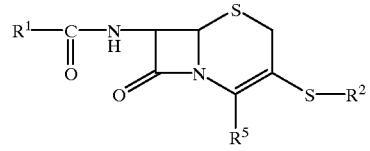

(Ia)

wherein

R¹ and R² are each as defined in claim 1, and

R⁵ is as defined above, or a salt thereof.

5. A compound of claim 1, wherein

R¹ is phenyl(lower)alkyl,

R² is thiazolyl substituted by carbamoyl(lower)alkyl, and

R³ is carboxy.

6. A pharmaceutical composition which comprises, as an active ingredient, a compound of claim 1 or a pharmaceutically acceptable salt thereof in admixture with pharmaceutically acceptable carriers or excipients.

7. A compound of claim 5, which is 7β-(2-Phenylacetamido)-3-(4-carbamoylmethylthiazolyl) thio-3-cephem-4-carboxylic acid.

* * * * *